US012339264B1

(12) United States Patent
Lowndes et al.

(10) Patent No.: US 12,339,264 B1
(45) Date of Patent: Jun. 24, 2025

(54) CALIBRATION FOR TUNEABLE DIODE LIDAR GAS DETECTION

(71) Applicant: QLM Technology Ltd, Paignton (GB)

(72) Inventors: David Leonard Dennis Lowndes, Bristol (GB); Xiao Ai, Bristol (GB); Alexander James Dunning, Bristol (GB)

(73) Assignee: QLM Technology Ltd, Paignton (GB)

( * ) Notice: Subject to any disclaimer, the term of this patent is extended or adjusted under 35 U.S.C. 154(b) by 0 days.

(21) Appl. No.: 18/786,245

(22) Filed: Jul. 26, 2024

(51) Int. Cl.
*G01N 33/00* (2006.01)
*G01N 21/17* (2006.01)
(Continued)

(52) U.S. Cl.
CPC ..... *G01N 33/0006* (2013.01); *G01N 21/3103* (2013.01); *G01N 21/39* (2013.01);
(Continued)

(58) Field of Classification Search
CPC ........... G01N 33/0006; G01N 21/3103; G01N 21/39; G01N 2021/1793; G01N 2021/399;
(Continued)

(56) References Cited

U.S. PATENT DOCUMENTS

| 3,069,654 | A | 12/1962 | Hough |
| 6,664,533 | B1 | 12/2003 | van der Laan et al. |

(Continued)

FOREIGN PATENT DOCUMENTS

| CA | 2630301 A1 * | 6/2007 | ............ G01N 21/39 |
| EP | 3956677 A1 | 2/2022 | |

(Continued)

OTHER PUBLICATIONS

R.O. Duda & P.E. Hart, "Use of the Hough transformation to detect lines and curves in pictures," Communications of the ACM, vol. 15 No. 1, pp. 11-15 (Jan. 1972). doi:10.1145/361237.361242.

(Continued)

*Primary Examiner* — John Fitzgerald
*Assistant Examiner* — Truong D Phan
(74) *Attorney, Agent, or Firm* — Haynes Beffel & Wolfeld LLP; Andrew L. Dunlap; Franklin M. Schellenberg

(57) ABSTRACT

Calibration methods for lidar equipment are disclosed. In some embodiments, the lidar equipment is provided with an internal gas reference cell with a known concentration of the gas of interest, such as methane ($CH_4$), which provides known absorptions at wavelengths particular to the gas. The lidar system laser beam passes through the gas reference cell before scanning a scene, and provides a known level of gas absorption at those known absorption wavelengths. This guarantees there is a minimum signal to be detected by the lidar system. In some embodiments, the lidar equipment is provided with an external calibration unit having one or more gas sample cells with predetermined lengths and known concentrations of the gas of interest. By making lidar measurements using an arrangement of these calibrated cells, adjustments to the parameters used in the algorithms relating detected photon counts with gas concentration may be made.

20 Claims, 14 Drawing Sheets

(51) Int. Cl.
  *G01N 21/31*  (2006.01)
  *G01N 21/39*  (2006.01)
  *G01S 7/497*  (2006.01)
  *G01S 17/88*  (2006.01)

(52) U.S. Cl.
  CPC .............. *G01S 7/497* (2013.01); *G01S 17/88* (2013.01); *G01N 2021/1793* (2013.01); *G01N 2021/399* (2013.01)

(58) Field of Classification Search
  CPC ....... G01N 21/274; G01S 7/497; G01S 17/88; G01S 3/023
  USPC ......................................... 73/1.03; 250/341.5
  See application file for complete search history.

(56) References Cited

U.S. PATENT DOCUMENTS

| | | | |
|---|---|---|---|
| 11,714,047 | B2 | 8/2023 | Ai et al. |
| 2003/0030001 | A1* | 2/2003 | Cooper ................ G01N 21/538 359/341.1 |
| 2007/0061114 | A1 | 3/2007 | Kalayeh |
| 2016/0084945 | A1 | 3/2016 | Rodrigo et al. |
| 2016/0334507 | A1 | 11/2016 | Hangauer et al. |
| 2019/0376890 | A1 | 12/2019 | Bennett et al. |
| 2022/0244179 | A1 | 8/2022 | Ai et al. |
| 2022/0390360 | A1 | 12/2022 | Ai et al. |
| 2022/0390361 | A1 | 12/2022 | Ai et al. |
| 2022/0390566 | A1 | 12/2022 | Ai et al. |

FOREIGN PATENT DOCUMENTS

| | | |
|---|---|---|
| GB | 2586075 B | 7/2021 |
| WO | 2005047871 A2 | 5/2005 |
| WO | 2014180483 A1 | 11/2014 |
| WO | 2021023971 A1 | 2/2021 |

OTHER PUBLICATIONS

D.H. Ballard, "Generalizing the Hough Transform to Detect Arbitrary Shapes", Pattern Recognition vol. 13, No. 2 pp. 111-122, 1981. doi:10.1016/0031-3203(81)90009-1.

H.K. Yuen et al., "Comparative study of Hough Transform methods for circle finding" Image and Vision Computing vol. 8 No. 1, pp. 71-77 (Feb. 1990). doi:10.1016/0262-8856(90)90059-E.

Harvey Rhody, "Lecture 10: Hough Circle Transform" Rochester Institute of Technology Lecture Notes Oct. 11, 2005 (22 pages). Downloaded from www.cis.rit.edu/class/simg782/lectures/lecture_10/lec782_05_10 on Feb. 13, 2025.

"Circle Detection using OpenCV | Python" Last updated Jan. 4, 2023 (6 pages) From the Open Source Computer Vision Library; Downloaded from wwwgeeksforgeeks.org/circle-detection-using-opencv-python/ on Feb. 13, 2025

Titchener et al., "Single photon Lidar gas imagers for practical and widespread continuous methane monitoring", Applied Energy, vol. 306, 118086, Oct. 31, 2021, 11 pages.

Pérez-Serrano et al., Atmospheric CO2 remote sensing system based on high brightness semiconductor lasers and single photon counting detection, Proc. SPIE 9645, Lidar Technologies, Techniques, and Measurements for Atmospheric Remote Sensing XI, 964503, Oct. 20, 2015, 11 pages (downloaded from https://www.spiedigitallibrary.org/conference-proceedings-of-spie on Oct. 20, 2023).

Van Well et al., "An open-path, hand-held laser system for the detection of methane gas", Institute of Physics Publishing, Journal of Optics A: Pure And Applied Optics, May 13, 2005, vol. 7, pp. S420-S424, doi:10.1088/1464-4258/7/6/025.

Golston et al., "Lightweight mid-infrared methane sensor for unmanned aerial systems", Applied Physics B Lasers and Optics, May 19, 2017, vol. 123, No. 170, pp. 1-9, doi: 10.1007/s00340-017-6735-6.

Gardiner et al., "Field Validation of Remote Sensing Methane Emission Measurements", Remote Sensing, MDPI, Sep. 14, 2017, vol. 9, No. 9:956, doi: 10.3390/rs9090956, 10 pages.

Wainner et al., "Scanning, standoff TDLAS leak imaging and quantification", Next-Generation Spectroscopic Technologies X, Proc. SPIE 10210, 1021006, 2017, doi: 10.1117/12.2264799, 11 pages.

Yang et al., "Natural Gas Fugitive Leak Detection Using an Unmanned Aerial Vehicle: Measurement System Description and Mass Balance Approach", Atmosphere, MDPI, Oct. 1, 2018, vol. 9, No. 9:383, doi: 10.3390/atmos9100383, 22 pages.

Sandsten et al., "Real-time gas-correlation imaging employing thermal background radiation", Optics Express 92, Feb. 14, 2000, vol. 6, No. 4, 12 pages.

* cited by examiner

CALIBRATION FOR TUNEABLE DIODE LIDAR GAS DETECTION

RELATED APPLICATIONS

This application is related to the commonly owned U.S. patent application Ser. No. 17/615,790, filed on Dec. 1, 2021, and U.S. patent application Ser. No. 18/384,269, filed Oct. 26, 2023, both entitled "RAPIDLY TUNABLE DIODE LIDAR," and both claiming priority from PCT Application PCT/GB2020/051816, which in turn claims priority to GB Patent Application GB 1911081.6, filed Aug. 8, 2019, now issued as GB Patent GB 2586075 B; all of which are incorporated by reference herein in their entirety for all purposes.

This application is also related to the commonly owned US Patent Application No. U.S. Ser. No. 17/663,102, filed on May 12, 2022, and entitled "OPTICAL ASSEMBLY FOR LIDAR DETECTION SYSTEM," which claims the benefit of U.S. Provisional Application No. 63/202,378 filed on Jun. 8, 2021, and entitled "OPTICAL TRANSCEIVER ARRANGEMENT FOR GAS LIDAR DETECTION SYSTEM," which are all hereby incorporated by reference herein in their entirety for all purposes.

This application is also related to the commonly owned US Patent Application No. U.S. Ser. No. 17/811,317, filed on Jul. 8, 2022 and entitled "METHOD OF OPERATING A LIDAR SYSTEM FOR DETECTION OF GAS," now issued as U.S. Pat. No. 11,644,576, which is a continuation of US Patent Application No. U.S. Ser. No. 17/806,039, filed on Jun. 8, 2022 and entitled "METHOD OF OPERATING A LIDAR SYSTEM FOR DETECTION OF GAS," now abandoned, which claims the benefit of U.S. Provisional Application No. 63/202,375 filed on Jun. 8, 2021, and entitled "METHOD OF SCANNING IN A LASER LIDAR SYSTEM," which are all hereby incorporated by reference herein in their entirety for all purposes.

This application is also related to the commonly owned US Patent Application No. U.S. Ser. No. 17/811,223, filed on Jul. 7, 2022 and issued as U.S. Pat. No. 11,714,047 on Aug. 1, 2023, entitled "METHOD TO DETERMINE GAS ABSORPTION IN RAPIDLY TUNED DIODE LIDAR," which claims priority to US Patent Application No. U.S. Ser. No. 17/805,937, filed on Jun. 8, 2022, entitled "METHOD TO DETERMINE GAS ABSORPTION IN RAPIDLY TUNED DIODE LIDAR," now abandoned, and which claims the benefit of U.S. Provisional Application No. 63/202,377 filed on Jun. 8, 2021, and entitled "METHOD TO DETERMINE GAS ABSORPTION IN RAPIDLY TUNED DIODE LIDAR," which are all hereby incorporated by reference herein in their entirety for all purposes.

FIELD OF THE TECHNOLOGY DISCLOSED

The technology disclosed relates to the use of lidar to determine gas concentrations, and in particular the calibration of lidar equipment incorporating diode lasers for the detection of methane gas.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves may also correspond to implementations of the claimed technology.

To monitor and control the release of greenhouse gasses such as methane ($CH_4$), systems that can remotely detect the presence and concentration of these gasses are installed in refineries, along pipeline installations, or even surveyed from aircraft or satellites.

However, if the results of these gas monitors are to be believed, they must produce accurate results. A false positive indicating a methane leak along a pipeline may initiate a costly repair operation, only for the crew to find the signal indicates a drifting breeze from a nearby animal facility. With the initiation of stricter regulation for methane releases in the European Union and the United States, inaccurate reporting of methane releases can have costly consequences for a company that in fact may be doing nothing wrong.

There is therefore a need for methods and systems to accurately calibrate remote sensing equipment for gas detection, both when initiating the equipment, and when installed in the field.

BRIEF SUMMARY

The technology disclosed provides methods and systems for accurate calibration of equipment for remote gas detection, and in particular for gas detection using lidar.

In some embodiments, the lidar equipment is provided with an internal gas reference cell that contains a known concentration of the gas of interest, and therefore provides known absorptions at wavelengths particular to the gas of interest. The laser beam of the lidar system passes through the gas cell before proceeding outside of the lidar system, and therefore provides a known level of gas absorption at those known absorption wavelengths. This guarantees that there is a minimum spectroscopic signal to be detected by the lidar system.

If more than the minimum expected absorption signal is detected, there can be assumed to be additional gas of interest in the laser beam path. If the minimum expected signal from the gas reference cell is detected, it may then be concluded that there is no additional gas of interest in the beam path. If there is an indication of some absorption, but at values less than the minimum expected signal, then a warning can be sent that the detection unit is out of calibration. And if no signal is detected at all, it may indicate the laser wavelength range has drifted, and temperature adjustment or replacement of components may be needed.

In some embodiments, the lidar equipment is positioned to collect lidar data with one or more external gas sample cells, each having a predetermined length and containing a known concentration of the gas of interest. These cells therefore also provide a source of predictable absorptions at wavelengths particular to the gas of interest. By making lidar measurements using an arrangement of these calibrated cells, adjustments to the parameters used in the algorithms relating detected photon counts with gas concentration may be made.

In particular, a fit for the concentration path length (CPL) that best matches the known concentrations in the remote gas cells may be computed. Once the calibration parameters have been adjusted to produce the expected results for the known cells, measurements in the field can be more accurately made using these adjusted parameters.

In some embodiments, additional image processing for lidar data collected from the calibration unit containing the gas sample cells may be made. In particular, the gas cells may be "tagged" using particular markers, such as a reflective tape, bar codes, or QR codes, that allow image processing algorithms to ignore certain portions of the data as not being related to lidar laser light passing through the sample cells containing the gas of interest. Algorithms that allow only image data from the gas cells to be used in the calibration procedure may be implemented as part of the calibration procedures.

The techniques disclosed herein may be used in the detection any gas of interest, but may be particularly useful for detection of methane ($CH_4$) which has an absorption feature at approximately 1651 nm, coincident with commercially available diode lasers.

Particular aspects of the technology disclosed are described in the claims, specification and drawings.

BRIEF DESCRIPTION OF THE DRAWINGS

The disclosure will be understood more fully from the detailed description given below and from the accompanying figures of embodiments of the disclosure. The figures are used to provide knowledge and understanding of embodiments of the disclosure and do not limit the scope of the disclosure to these specific embodiments. Furthermore, the figures are not necessarily drawn to scale.

DETAILED DESCRIPTION

The following detailed description is made with reference to FIGS. 1-14. Exemplary implementations are described to illustrate the technology disclosed, not to limit its scope, which is defined by the claims. Those of ordinary skill in the art will recognize a variety of equivalent variations on the description that follows.

Tunable Diode Lidar

Remote lidar detection of gasses can be achieved by sending a laser beam encoded with both wavelength and amplitude modulations from a lidar transceiver into an environment in which the gas of interest may be present. Scattered photons from a remote point that return along the optical path to the transceiver can be analyzed for absorption at particular laser wavelengths corresponding to known absorption features for that gas. When reduced return photon counts from the remote scattering sites are detected at those gas wavelengths, the concentration of gas needed to produce that absorption along the optical path can be calculated.

Such a tunable diode lidar (TDLidar) system has been disclosed in the patent GB 2586075 B entitled "Rapidly Tunable Diode Lidar" and filed in the U.S. as patent application Ser. No. 17/615,790 and 18/384,269, all of which are incorporated herein by reference.

Figure 1:
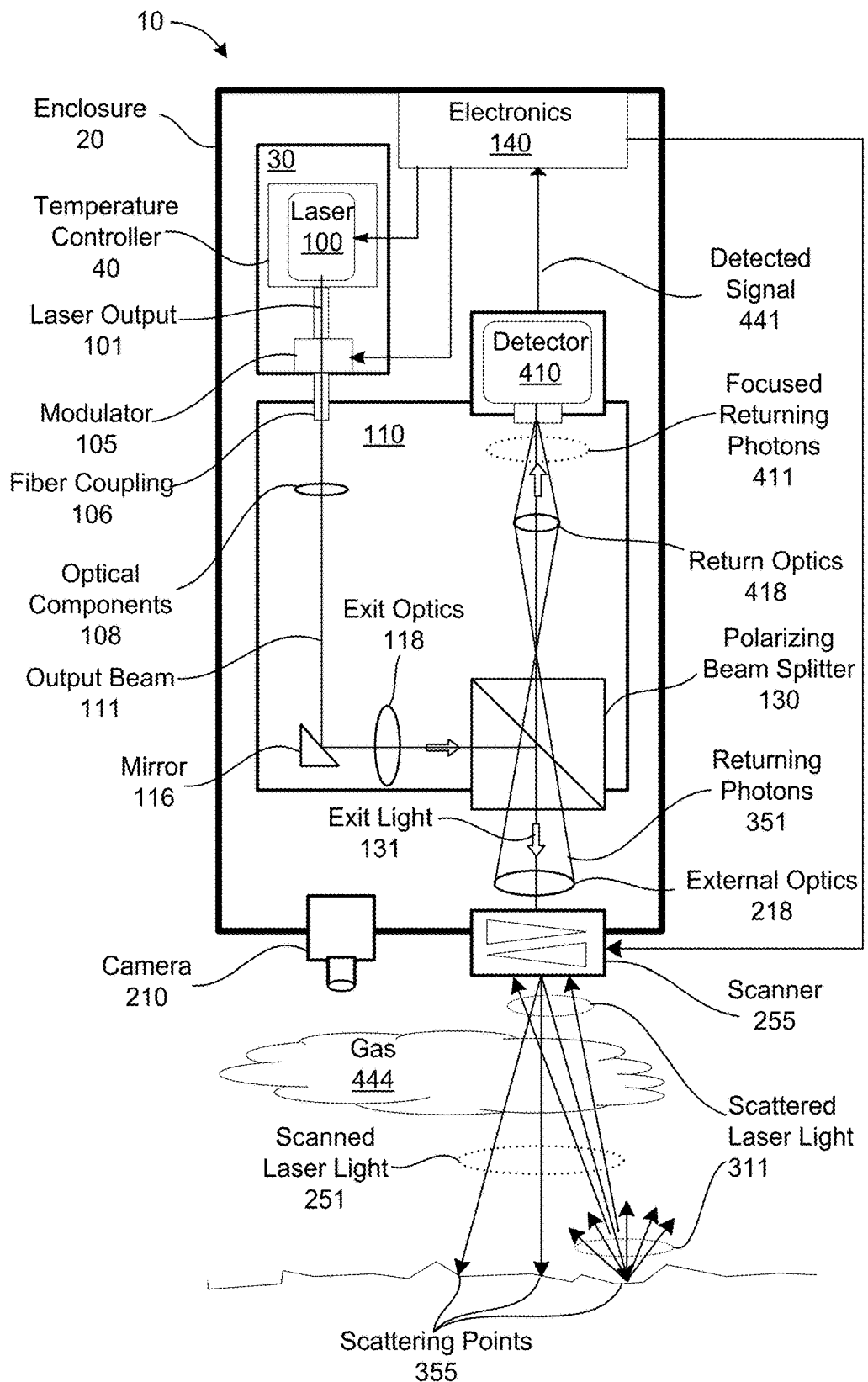
FIG. 1 illustrates schematic diagram of a lidar system according to an embodiment of the invention.

A schematic illustration of an example of a lidar system 10 to accomplish the remote lidar detection of a gas 444 is illustrated in FIG. 1. The system illustrated comprises an enclosure 20 containing: an optics assembly 30 that includes a laser 100, transceiver unit 110 that relays the laser output beam 111 to pass out of the lidar system 10 and to also collect light returning from a scene onto a detector 410; a scanner 255 to direct the beam to various locations within the scene, and electronics 140 to provide signals to the optics assembly 30 and laser 100, and to collect signals from the detector 410 and process them. In additional to the components for transmitting laser light and collecting return signals, a conventional camera 210 may also be provided in some embodiments. The camera 210 may be used to provide conventional visible or infrared imaging of the scene being scanned, and aid in adjustments for orientation and positioning of the lidar unit.

The laser light source 100 may be any laser capable of producing a continuous wave optical output at or near wavelengths corresponding to a gas absorption line of interest. One example is a multi-quantum well distributed feedback (DFB) diode laser. Such a laser may be operated at an eye-safe of output power of approximately 10 mW at a wavelength of $\lambda \approx 1651$ nm (corresponding to a well-known methane absorption line).

The output 101 from the laser 100 is driven by a current provided by control electronics 140. When the current is altered, the output wavelength changes, and so a periodic current scan has the effect of scanning the wavelength. A typical wavelength scan is achieved by scanning the current to the diode laser with a period of approximately 1 MHz. The current scan range needed to provide output encompassing the 1651 nm CH$_4$ absorption line (FWHM of approximately 50 pm) is approximately 60 mA.

The laser 100 may also have a temperature control device 40, typically a thermoelectric or Peltier cooler, that sets the overall temperature of the diode laser 100. For a typical system, the temperature control device 40 may be integrated into the laser device packaging, and the temperature set to be near or at ambient temperatures, but controlled to remain stable within +0.01° C.

The optical components of the optics assembly 30 may also include a number of fiber or fiber-coupled components, such as a polarizer, that control the properties of the laser output 101. A fiber coupled external optical modulator 105, such as a Semiconductor Optical Amplifier (SOA), which may be polarization-maintaining, will typically also be included in the optics assembly 30. In some configurations, this modulator 105 provides binary amplitude modulation (on/off) for the laser output 101, and this modulation may also be controlled by the electronic controller 140. In some configurations, the modulator 105 may also have a temperature controller, such as a thermoelectric cooler, to maintain stability and control of the modulation characteristics.

The output of the optics assembly 30 will typically be a fiber coupling 106 paired with additional free-space optical components 108 to produce a freely propagating collimated output beam 111 of laser light. In some configurations, the output beam 111 is both collimated and polarized.

The output beam 111 may then be reflected off a mirror 116 and pass through additional optical components (shown as exit optics 118) to modify the beam properties for transmission outside the enclosure 20. In the configuration illustrated, the exit from the enclosure 20 occurs by reflection off a polarizing beam splitter 130, which also serves as a window to the outside world. In other configurations, the polarizing beam splitter may be completely contained within the enclosure 20, and an additional external window used to transmit the laser output beam 111 out of the optical transceiver assembly.

Once laser light as an exit beam 131 has exited the enclosure 20, it may pass through additional external optics 218 that further shape and condition it. These optics may include a lens to collimate the divergent beam, additional polarization components, such as a quarter wave plate, to produce output that is circularly polarized. The output beam may also pass through an angular deflection system, such as a scanner 255, that directs the exit beam over a range of angles in two- and/or three-dimensions in an external scene to be measured. The scanning and beam deflection control may also be controlled by the electronics 140, and coordinated with the signals driving the laser drive current (and therefore the wavelength scan) and also the amplitude modulation.

In some embodiments, a Risley prism scanner may be used as the beam deflector, for which the full angular range is typically up to 0.5 radians in both x and y. Examples of optical components for the external optics and scanner are presented in more detail in U.S. patent application Ser. No. 17/811,317, which has been incorporated by reference in this Application in its entirety. However, any system of external optics that can systematically direct the laser output into the environment over a range of angles may be utilized.

The outgoing scanned laser light 251 will follow the beam path as directed by the scanner 255, and pass through the environment. In some situations, the exit beam may pass through some concentration of a gas 444 having absorption features for some of the wavelengths produced by the scanned laser. Eventually, the light may scatter off various scattering points 555 on various objects in the environment (trees, mountains, rocks, buildings, fences, etc.). Some of the scattered laser light 311 will be backscattered along the same path as the outgoing scanned laser light 251, encountering the scanner 255 and being collected by the external optics 218. This returning scattered light 311 will also pass through the gas 444, which can absorb additional light.

The scattering from the scattering points 555 in the environment is typically diffusive scattering, so the returning light will be much weaker than the outgoing light. Typically, only a tiny fraction of the scattered light (~$10^{-8}$) returns to the transmitting system. The returning photons pass through the scanner 255 again, and are therefore collinear with the initial source of the photons. However, as the photons have been back-reflected from the distant object, and if a quarter wave plate has been used in the external optics 218 to make the output scanned laser light 251 circularly polarized, the circular polarization state of the reflected photons 311 is now the opposite from the outbound photons. Once the counter-circularly polarized photons also pass through the quarter wave plate in the external optics 218 upon returning, the returning photons 351 will have a linear polarization orthogonal to the polarization of the exit laser light 131. Therefore, when entering the polarizing beam splitter 130, the returning photons 351 are not reflected, but pass through the polarizing beam splitter 130.

Internal return optics 418 then collect the returning photons 351 and direct the photons 411 into the detector 410. The detector 410 may be any photodetector that can detect weak amounts of light and even single photons, such as an avalanche photodiode or a single-photon avalanche diode (SPAD). The SPAD device may incorporate a passive quenching resistor as in a negative feedback avalanche diode (NFAD), or alternatively, be accompanied by active or passive avalanche quenching circuitry. In some implementations, the photodetector may take the form of an array of photodetectors, to enhance imaging capabilities or improve detection performance.

The detector 410 converts the detected photons into a detected signal 441, which may then be processed electronically. The processing may include being recorded and analyzed by the same electronics 140 used to drive the laser 100 and modulator 105, or may be recorded and analyzed by a separate set of electronics. However, some degree of processing to analyze the detected signals 441 from the detector 410 and correlate them with the signals from the electronics 140 used to drive the laser current and to control the modulator 105 will typically be used.

In the normal course of operations, the laser current is scanned so that the wavelength range encompasses a gas absorption feature, and the modulator applies a binary pseudo-random intensity modulation to the outbound beam, allowing correlation of the detected signal with the applied pseudo-random modulation to confirm the intensity of the returning photons as being from the laser source and not some outside source of other photons.

Ideally, as the laser wavelength is scanned over the wavelength range corresponding to an absorption feature of a gas, and a reduction in the return signal will be observed when the laser is operating at the gas absorption wavelength but not on either side of the absorption wavelength. Detection of a reduction in returning scattered laser light can, however, be indicative of several things, including temporary obstruction of the optical path by birds, passing smoke, or even a brief failure of the transmitter.

Variations in signal may be caused by several external factors other than presence of gas, such as varying object distances and reflectivity, and varying weather conditions including fog and snow. Such variations in signal are not spectroscopically selective in the same way as gas absorption, and so are largely not manifested as variations in measured CPL. However, biases in the measured gas CPL can occur when these external signal variations are combined with non-linearities and saturation effects in the detector. To remove this signal bias effect, compensation mechanisms are applied, whereby detection signals are scaled or weighted, according to, for example, the measured count rate or inter-arrival time of detection events.

To be certain that the detected reductions in photon counts are related to absorption from the gas of interest, and additionally to be able to determine the correct concentrations for the gas of interest, some kind of calibration procedure for the lidar system is desired.

One way to achieve calibration of a Lidar system is by having an internal gas reference cell containing a known concentration of the gas of interest available. Detection of absorption of the gas in the reference cell serves as a reference absorption within the lidar system. In some systems, portions of a laser beam are diverted to pass through a reference cell, providing confirmation that the laser is operating at the desired spectral feature. However, such systems require a second set of detectors for the light through the reference cell, and reduce the intensity available to send into the scene for lidar detection.

Instead, a gas reference cell may be placed directly in the laser beam before it exits the lidar unit. When all is operating normally, the presence of the absorption from the reference cell ensures that is always a signal of some sort to detect, regardless of whether the gas of interest is present in the environment. The absence of a signal from the internal cell, which may be due to the lidar system operating at an incorrect or offset wavelength, can also be used as a diagnostic signal to indicate a problem. The error signal this can provide can be used to adjust the operating conditions of the laser, bringing the laser wavelength scanning range into correspondence with the absorption feature for the gas of interest.

Another way to achieve calibration of a Lidar system is by having one or more external gas sample cells containing a known concentration of the gas of interest available that may serve as a reference absorption within a lidar image. Testing the system with known absorbers in the environment having known dimensions and known concentrations of gas placed in the field of view of the lidar system guarantees there should be a signal to detect. The return lidar signals from these external gas sample cells can be used to fit the calibration parameters used by the algorithms that analyze the lidar data, so that the return signals are well matched to the known gas concentrations for the cells. The fitted parameters can then be used with the lidar system when out in the field, measuring new situations Embodiments comprising these options will now be described in detail.

Internal Calibration

Figure 2:
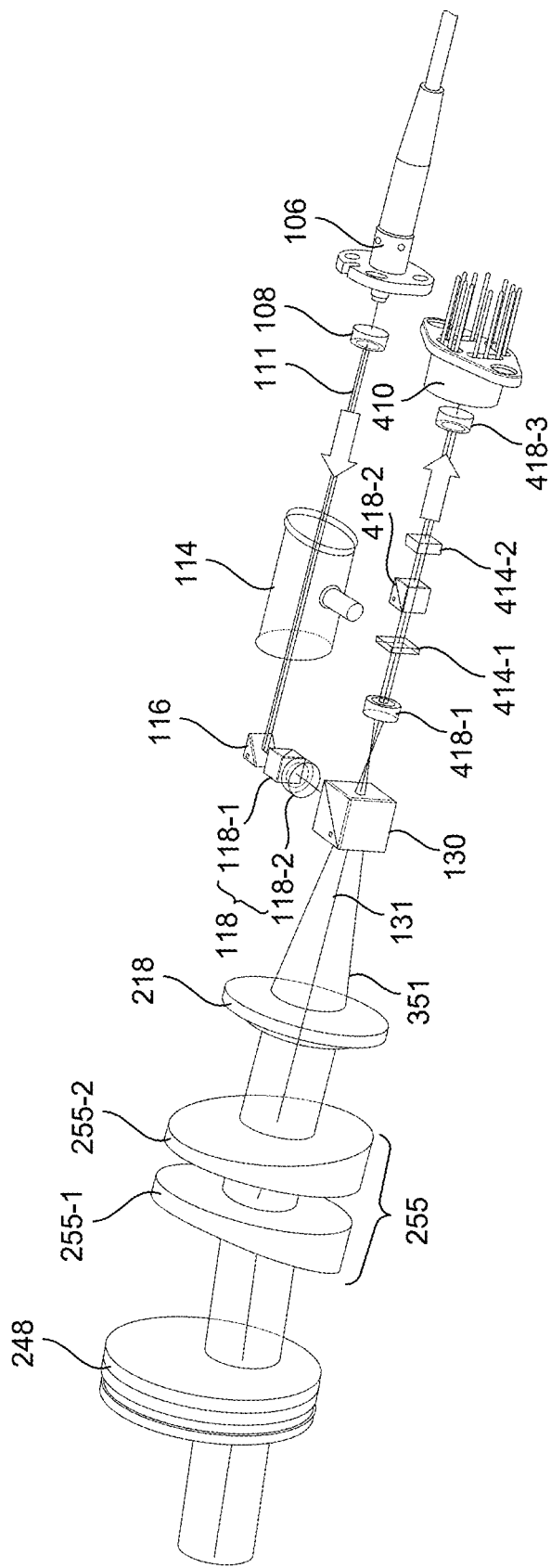
FIG. 2 illustrates a schematic diagram of components of a lidar system according to an embodiment of the invention.

A representative optical layout of the optical components for an embodiment of a TDLidar transceiver system is shown in FIG. 2. The laser light source 100 (outside the components shown in FIG. 2) may be any laser capable of producing a continuous wave optical output at or near wavelengths corresponding to the gas absorption line of interest. The laser output may be fiber coupled to packaging that may include various optical components, including an amplitude modulator 105 (also outside the components of FIG. 2), and the modulated laser light will end up in a fiber coupler 106 that allows the laser light to propagate in free space. Collimating optics 108 may be used to additionally shape and form the output beam 111 for free-space propagation.

The embodiment of FIG. 2 is shown having an internal gas reference cell 114 for calibration. As illustrated in FIG. 2, the laser output beam 111 passes through two windows on opposite sides of the gas reference cell 114. The gas reference cell contains a sample of the gas of interest, for example, methane ($CH_4$) or carbon dioxide ($CO_2$). The cell, described in more detail below, is typically filled with a known, calibrated concentration of the gas of interest, and has a known and calibrated length between the centers of the windows. The windows may be optically polished elements that are non-parallel, and the two windows may also be arranged to have a counter-angled wedge configuration, to reduce multi-reflection interference effects, as described in more detail below. The windows may additionally be coated with anti-reflection (AR) coatings to further reduce reflections and possible interference effects.

The additional components illustrated in the embodiment of FIG. 2 are a mirror 116, which reflects the laser output beam 111 through exit optics 118, which, in this example, comprise a polarizer 118-1 and additional lens 118-2 but may also comprise other or additional beam shaping optics. In some embodiments, the mirror 116 may be replaced with a polarizing reflector to further define the polarization state of the output beam 111.

Next, as was also shown in FIG. 1, after the exit optics 118 the laser beam enters a polarizing beamsplitter 130 with a polarization state such that the laser beam is reflected towards the output optics 218. In some embodiments such as those illustrated in FIGS. 1 and 2, the polarizing beamsplitter also serves as a window in the enclosure 20, allowing the laser output beam 111 to pass out of the TDLidar enclosure 20 as an exit beam 131. The external optics 218 may comprise telescope components that additionally collimate or shape the transmitted laser light, but can be any combination of optical elements that shape the outgoing laser light to the desired profile.

Also shown are components of a scanner 255 which may comprise two prisms 255-1 and 255-2 arranged as a Risley prism scanner, to direct the output beam over a variety of angles in two-dimensional or three-dimensional scans of a scene.

Finally, before transmitting the laser light into the scene to be scanned, the beam may pass through a polarization component 248. This can be any variety of polarizing optical elements, but will typically comprise a quarter wave plate, so the outgoing light is converted from linear polarization into circular polarization. When reflected from a distant scattering point, the circularity of the polarization will be reversed, and upon passing back through the polarization component 248, the circular polarization is converted to linearly polarized light orthogonal to the original outgoing polarization. This means that the returning scattered laser light 351 will now be completely transmitted through the polarizing beamsplitter, and be directed towards the detector 410.

FIG. 2 also shows the return optics 418 with additional detail, with a lens 418-1 to collect and possibly collimate the returning light, a polarizer 418-2 to allow only light orthogonal to the outgoing light to be transmitted to the detector 410, and a focusing lens 418-3 to collect and focus the returning photons 411 onto the detector 410. Additionally, wavelength and/or optical filters 414-1 and 414-2 selected for the nominal wavelength range of the diode laser may also be used to allow only the scattered diode laser light back into the system to reach the detector.

Figure 3:
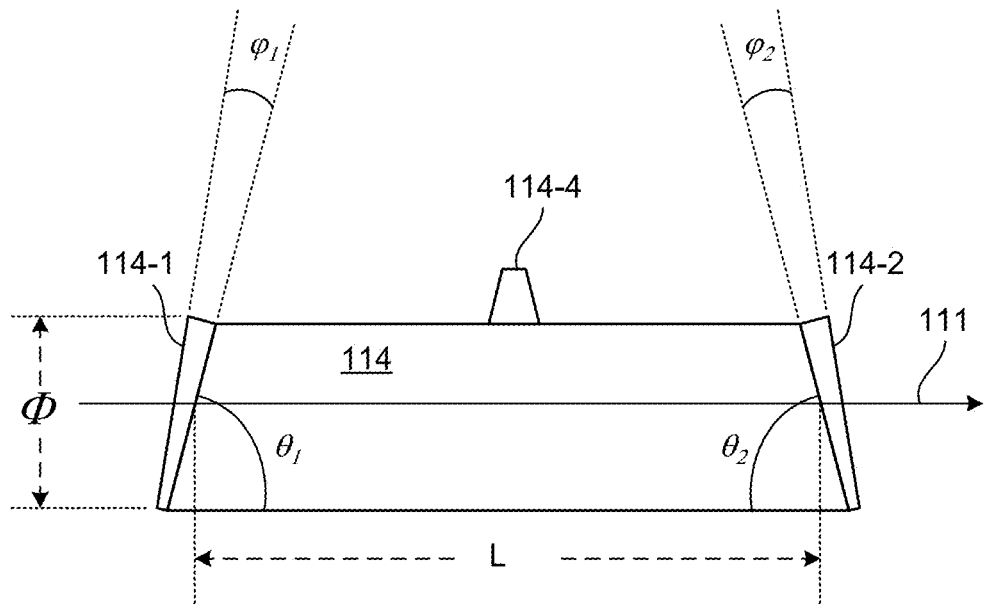
FIG. 3 illustrates a diagram of a gas reference cell as may be used for internal calibration in embodiments of the invention, such as those illustrated in FIGS. 1 and 2.

FIG. 3 illustrates a cross section view of a gas reference cell 114 that may be used in some embodiments. Typical gas cells are roughly cylindrical in shape, with a diameter Φ on the order of ≈1 cm and a length L of a few centimeters. Representative dimensions for the gas reference cell as may be used in some embodiments are presented in Table I below.

TABLE I

Representative Gas Reference Cell Parameters.
Gas Reference Cell Dimensions

| | |
|---|---|
| Length L | 5.0 ± 0.1 cm |
| Outer Diameter Φ | 12 mm |
| Clear Aperture | 9 mm |
| Window Thickness | 1.5 mm |
| dow Angle $\theta_1$ | 87.0 degrees |
| Exit Window Angle $\theta_2$ | −87.0 degrees |
| Entrance Window Wedge $\varphi_1$ | 0.3 degrees |
| Exit Window Wedge $\varphi_2$ | 0.3 degrees |

In some embodiments, the gas reference cell may be fabricated using soda lime glass, but any number of materials may be used. The gas reference cell 114 may be constructed such that it has two windows, an entrance window 114-1 and an exit window 114-2, fabricated of higher quality optical glass or quartz, and sealed to the reference cell with UV-curing, thermal-curing, or multi-part-curing material. The gas cell 114 may be typically positioned such that the laser output beam 111 passes through the center of the entrance window 114-1 and the center of the exit window 114-2. The distance between the inner surface centers of the entrance and exit windows 114-1 and 114-2 may be a predetermined length L, typically measured in cm.

In some embodiments, the windows 114-1 and 114-2 may be fabricated from a higher quality optical material, such as 8270 glass. In some embodiments, the windows 114-1 and 114-2 may be arranged relative to the laser beam path to be beveled or, as illustrated in FIG. 3, counter-beveled, to further reduce the possibility of etalon interference effects. As illustrated, the entrance window is beveled at an angle $\theta_1$ while the exit window 114-2 is beveled at an angle of $\theta_2$. In some embodiments, $\theta_1 = -\theta_2$. In some embodiments, the windows may be coated with anti-reflection (AR) coatings. In some embodiments, the AR coatings may be fabricated using magnesium fluoride ($MgF_2$).

In addition to beveling (or counter-beveling) the windows of the gas reference cell 114, the windows 114-1, 114-2 may also be wedged, again to avoid etalon interference effects. For the embodiment illustrated in FIG. 3, wedge angles $\varphi_1$ and $\varphi_2$ are shown. For some embodiments, $\varphi_1 \approx \varphi_2 \approx 0.3$ degrees. For some embodiments, $\varphi_1$ and/or $\varphi_2$ may be greater than 0.2 degrees.

The gas reference cell 114 may be filled with a predetermined amount of a reference gas at a predetermined partial pressure through a stem 114-4, and then sealed. In some embodiments, the gas in the gas reference cell may be a mixture of 5% methane ($CH_4$) and 95% nitrogen ($N_2$) at a total pressure of 740 Torr. In some embodiments, the gas reference cell may be filled and sealed with a gas concentration traceable to a gas mixture standard, such as those provided by the National Institute of Standards and Technology (NIST). In some embodiments, instead of a sealed stem, a fill port including a stopcock may be provided to connect the cell with a gas supply line, which allows the gas concentrations to be varied or replenished.

When the diode laser is scanned in wavelength over time through a range that nominally corresponds to an absorption feature for the gas to be detected, absorption from the gas at the absorption wavelengths should produce a detectable dip in the return signal (i.e., a reduction in intensity for the return signal when absorption is higher). This dip will be detected regardless of whether any additional gas is present in the outgoing and returning beam path. As a practical matter, the various time scans of wavelength are correlated to electronic detection time "bins" that count photons when the laser is nominally within a certain subset of the wavelength scan. The integrated time bins for the detected signal can be aligned to the corresponding diode laser wavelength.

Figure 4:
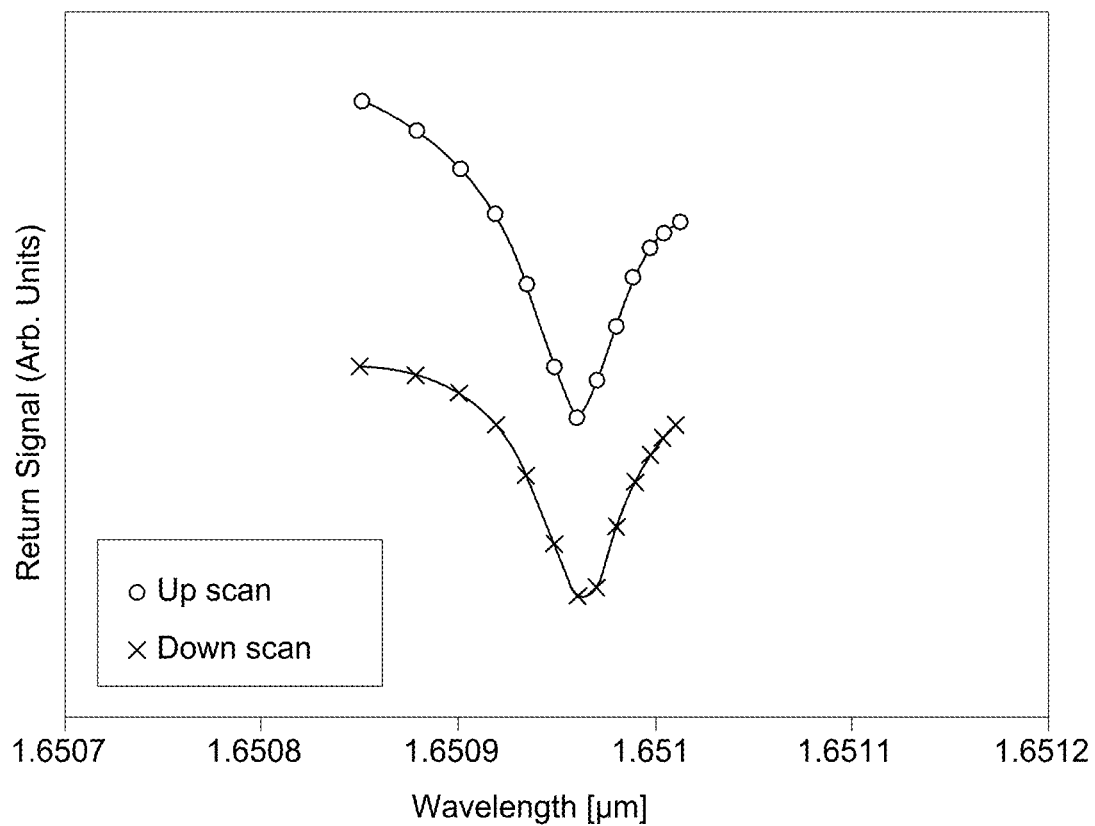
FIG. 4 illustrates a plot of photon count signals collected on both an upward wavelength scan and a downward wavelength scan for a lidar system detecting methane according to an embodiment of the invention.

FIG. 4 shows an example of rapidly tunable diode laser absorption spectra for methane ($CH_4$) converted from scan time bin ($\tau_i$) to wavelength. By matching the detected dip shape to known $CH_4$ line shape from a HiTRAN (high-resolution transmission molecular absorption) database, as is further described in U.S. patent application Ser. No. 17/811,223, which has been incorporated by reference in its entirety, a minimum "dip" in the return signal can be identified. Note that the scan during the increasing wavelength portion of the scan (the "Up scan") is not identical to the scan during the decreasing wavelength portion of the scan (the "Down scan"). However, both have dips in signal at the time bin corresponding to the wavelength for methane absorption.

Figure 5A:
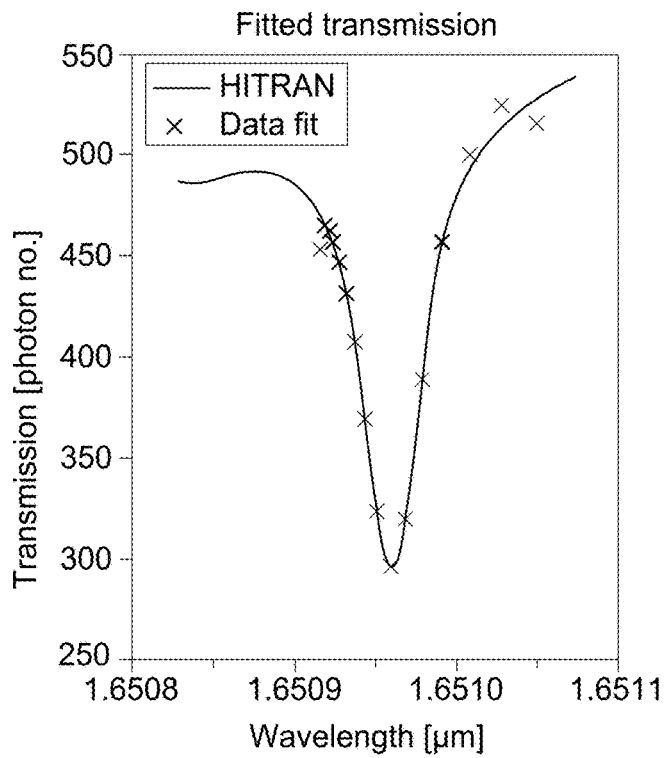
FIG. 5A illustrates a plot of photon count signals vs. wavelength and FIG. 5B the data of FIG. 5A converted into an attenuation cross-section in $(ppm \times m)^{-1}$ for methane data collected using for a lidar system according to an embodiment of the invention.
Figure 5B:
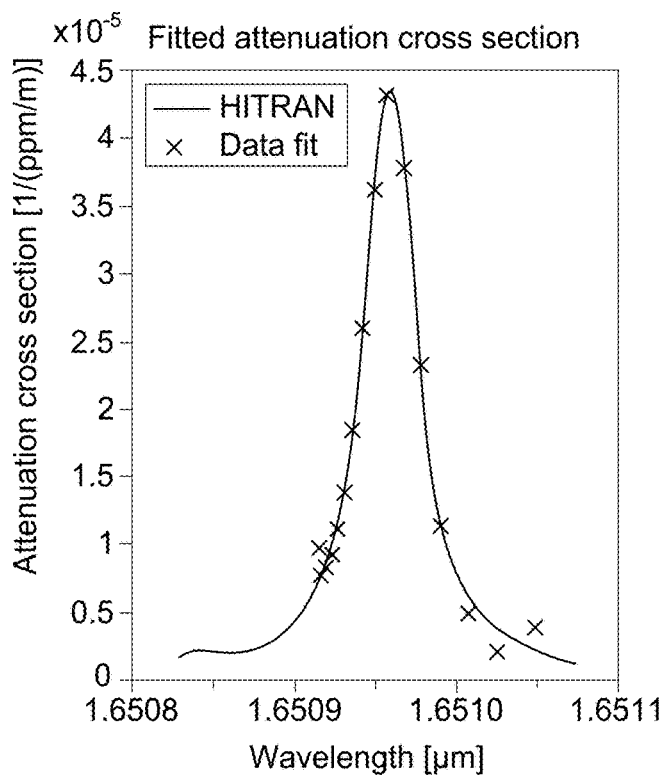

FIGS. 5A and 5B show measurement results fitted to HiTRAN data. The graph in FIG. 5A shows the output of the instrument function (black line) optimized to match the sensor data (crosses). The graph of FIG. 5B shows the HiTRAN attenuation cross section with the raw data. The optimization of the instrument function parameters also gives the information about the amplitude, slope and gas absorption in the spectrum. This allows one to accurately plot the spectral transmission vs. wavelength, as shown in the plot of FIG. 5A. Here, the black line is the transmission estimated by the instrument function, while the crosses are the raw measurement data used for the optimization/calibration.

The plot of FIG. 5B is similar, but instead of showing the transmission, it shows the attenuation cross-section as a function of wavelength. The black line is the attenuation cross section data taken directly from HiTRAN, i.e. $\sigma(\lambda)$. The crosses are the raw measurement data, but transformed from transmission to attenuation cross section using the instrument function equation in reverse.

This method allows one to accurately calibrate the wavelength and other measurement parameters of a rapidly tunable diode lidar gas sensor.

The illustrations of FIGS. 4 and 5 both show a preferred situation in which the wavelength dip from the absorption feature of the gas of interest is in the middle of the wavelength scan, i.e. approximately centered in the scan within ±10% of the scan range from the center position. However, as environmental conditions (such as temperature, altitude/pressure, etc.) change, the center of the nominal diode laser wavelength scan may not be coincident with the gas absorption feature from the gas reference cell.

Figure 6A:
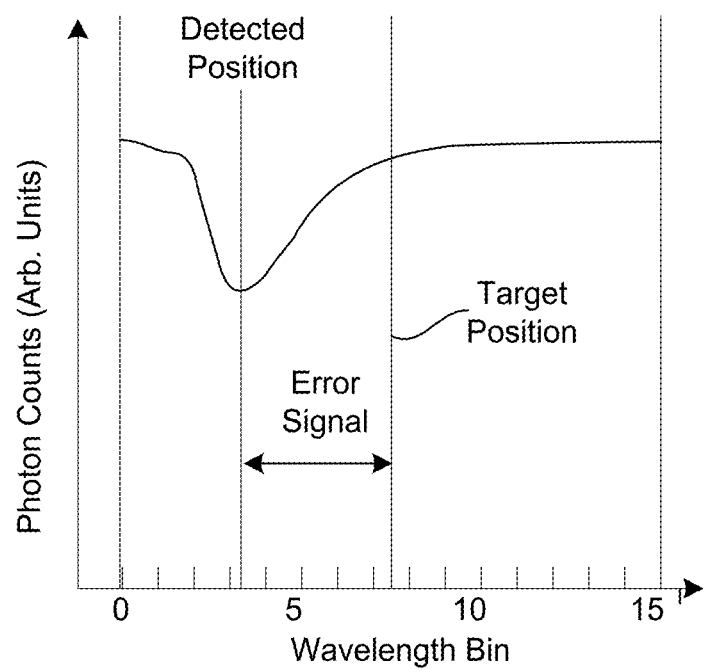
FIG. 6A illustrates a representative plot of photon count vs. wavelength bin when the error signal is non-zero.

This is illustrated in FIG. 6A, where a large "error signal" is detected as the minimum return signal is offset from the target wavelength bin. But by changing the temperature of the diode laser, the center of the diode laser wavelength scan can be changed, and better aligned with the center of the absorption feature from the gas in the gas reference cell, reducing the "error signal" to be approximately 0.

Figure 6B:
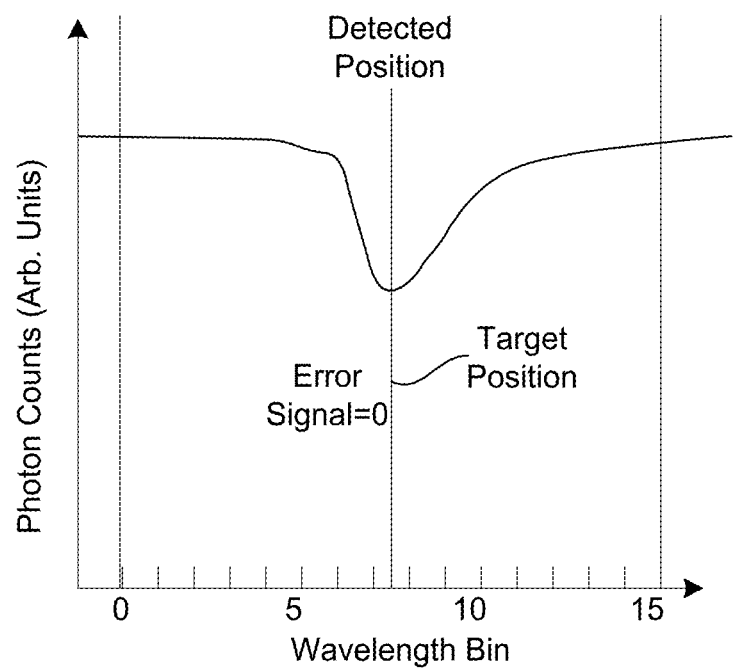
FIG. 6B illustrates a representative plot of photon count vs. wavelength bin after adjusting the diode laser temperature.

To this end, as was illustrated in FIG. 1, the diode laser 100 may be mounted on a temperature controller 40, such as Peltier cooler/heater. When an error signal is detected, as illustrated in FIG. 6A, the temperature of the temperature controller may be changed to heat or cool the diode laser until the detected dip due to absorption occurs in the center of the diode laser wavelength scan, as is illustrated in FIG. 6B.

Because there is a gas reference cell 114 with some level of absorption (e.g. ~5%) always present in the output beam path, the system will always detect a dip in the returning signal of at least that magnitude whether or not gas is present in the external environment. If there is gas in the gas reference cell but no dip detected, then a likely conclusion is that the laser wavelength is incorrectly set, and corrective action should be taken.

Figure 7:
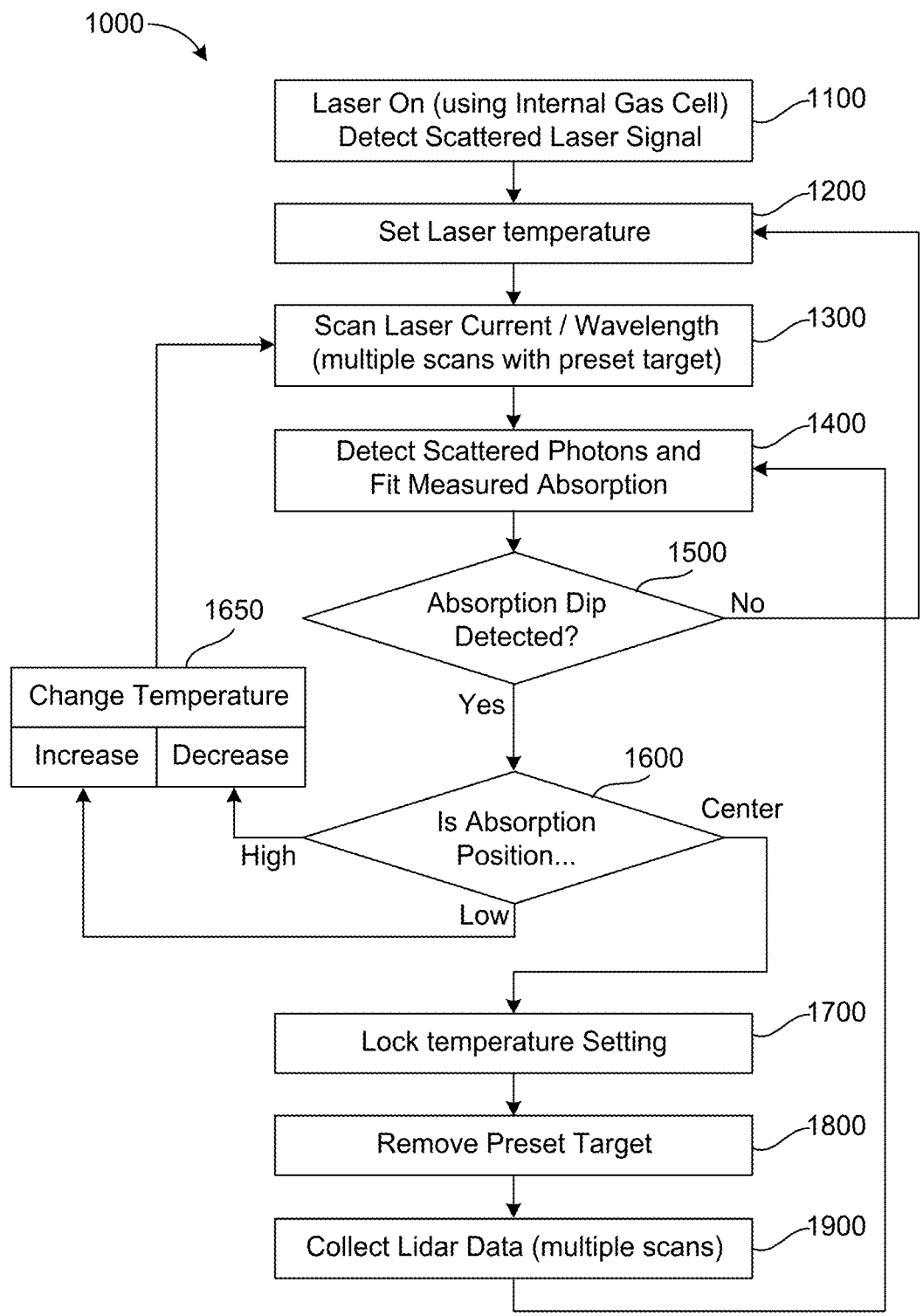
FIG. 7 illustrates a flow chart for a method of adjusting the diode laser operating temperature to center the wavelength scanning range around an absorption line for a gas of interest.

An exemplary a process 1000 to provide temperature tuning to match diode wavelength scans to the absorption of a gas reference cell by reducing the error signal is presented in the flow chart of FIG. 7.

In the first operation 1100, the laser of the lidar system is turned on and laser output passes through the gas reference cell and through the optical system to exit the lidar system. In some embodiments, a preset target, such as a rigid board or cardboard sheet, is placed some distance away to provide a scattering site that returns a signal to the lidar system to be collected on the detector. In other embodiments, scattering sites within a scene may provide enough return light, such that a separate scattering target may not be needed. As part of this initialization operation, an initial scattered laser signal from the scene may be detected and confirmed, to be certain that the system is aligned correctly.

In the next operation 1200 (which may initially be concurrent with initializing the system in operation 1100), a temperature is set for the diode laser, using the cooling/heating system.

In the next operation 1300, the drive current for the diode laser is then scanned, having the effect of scanning the laser wavelength over a wavelength range, or spectrum of wavelengths. Single scans over a designated, predetermined wavelength range may be used, or multiple and/or repeated scans may be used. The scan is typically carried our such that points of time of the scan have a predetermined relationship to the drive current and the spectrum of wavelengths.

In the next operation 1400, the detector signal from the returning scattered photons over a period of time as the wavelength is scanned is measured and processed (as, for example, was illustrated in FIGS. 4 and 5).

Figure 8:
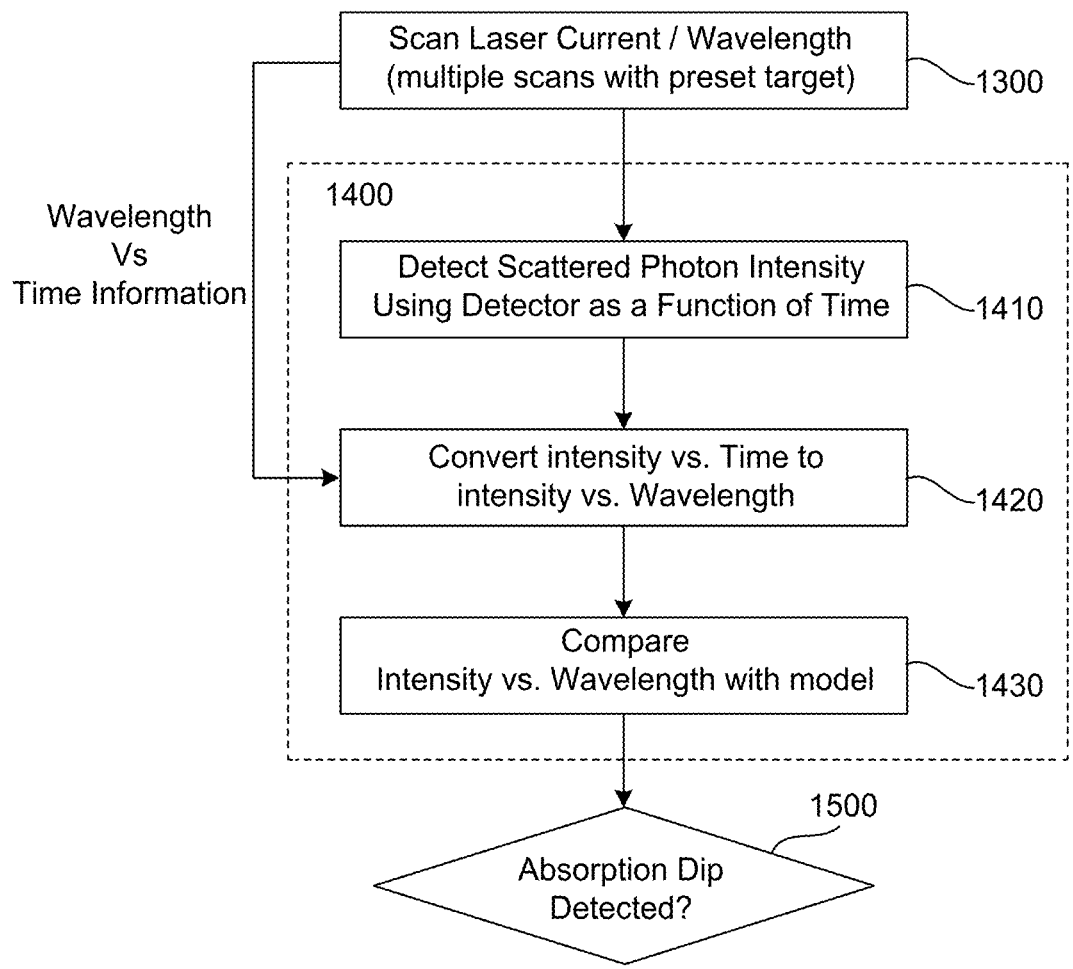
FIG. 8 illustrates a detailed flow chart for a fitting procedure as used in the method illustrated in FIG. 7.

Actions that may be taken in executing operation 1400 are further illustrated in FIG. 8. In the initial operation 1410 of operation 1400, the returning scattered diode laser photon intensity is measured as a function of time. In the next operation 1420 of operation 1400, the information on the wavelength scan is used to convert the photon intensity vs. time information into photon intensity vs. wavelength. In some embodiments, the axis will not be an absolute wavelength, but a "wavelength bin" in relative units, correlated with the current In the next operation 1430 of operation 1400, a comparison is made between the detected photon intensity data and a model for absorption, such as a Lorentzian function, or HiTRAN data stored in a database.

In the next operation 1500, shown in both FIGS. 7 and 8, the processed data is analyzed to see at which wavelength bin the absorption is the strongest (i.e. the return signal is the weakest), and to determine the presence of a reduction or "dip" in signal due to absorption, as was illustrated in FIGS. 4 and 5A. If no absorption dip at all is detected, the system then returns to operation 1200, adjusting the temperature of the diode laser over a range that may extend from +5° C. to +45° C., and the operations 1300-1500 are repeated and the temperature again adjusted until an absorption dip is detected.

Once an absorption dip is detected, in the next operation 1600, a determination is made as to the sign and magnitude of the "error signal" (as was illustrated in FIG. 6A).

If the absorption dip is not centered in the wavelength scan (either high or low), then the system proceeds to operation 1650, and the laser temperature controller is set to a somewhat different temperature (by either decreasing or increasing temperature, respectively), and the system returns to operation 1300 at the newly reset temperature. The process continues in making iterative adjustments to the temperature by repeating operations 1300 through 1500 until the error signal for the absorption dip is within a predetermined tolerance level (e.g., exactly centered in the wavelength scan, or at some pre-determined desired position along the wavelength axis).

If the absorption dip is within the tolerance level from the center of the wavelength scan, then the system proceeds to operation 1700, locking the temperature controller to the new temperature.

In the next operation 1800, laser light from the lidar system is directed to enter a scene to be observed. If a preset target or scattering object has been used, the preset target is removed.

In the next operation 1900, lidar data is collected for the scene to be observed.

It should be noted that, as lidar data is collected, the system will continuously scan the collected data for the absorption dip due to the gas reference cell (present in every scan, regardless of whether gas is present in the scene) as in operation 1400. When that absorption dip drifts from the center position, the corrective actions taken to adjust the temperature in operations 1500 through 1900 can be repeated continuously throughout operation, even while the lidar data is being collected.

External Calibration

Figure 9:
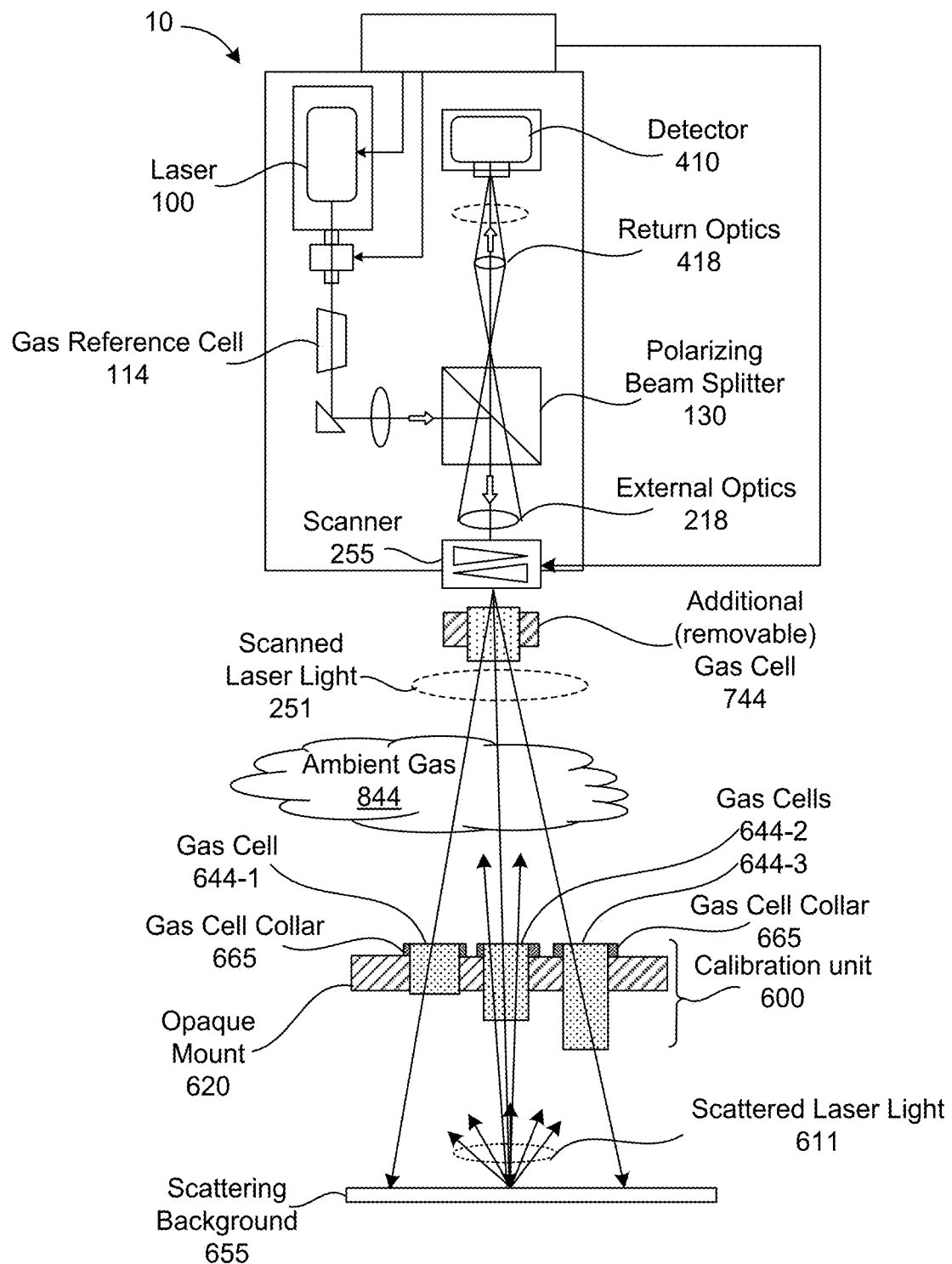
FIG. 9 illustrates a schematic diagram of a lidar calibration arrangement using external gas sample cells for calibration according to an embodiment of the invention.
Figure 10A:
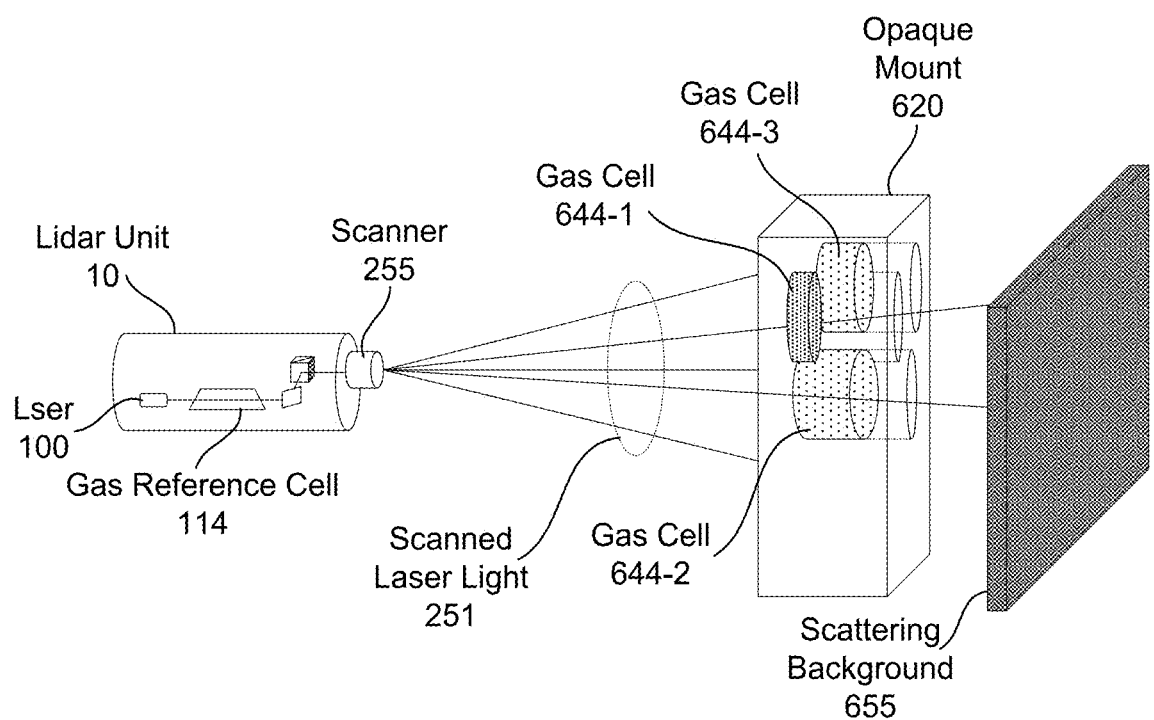
FIGS. 10A and 10B illustrate some of the components of the lidar arrangement of FIG. 9, with FIG. 10A illustrating three external gas sample cells for calibration, and FIG. 10B illustrating the three external gas sample cells of FIG. 10A along with an additional (removable) gas cell.
Figure 10B:
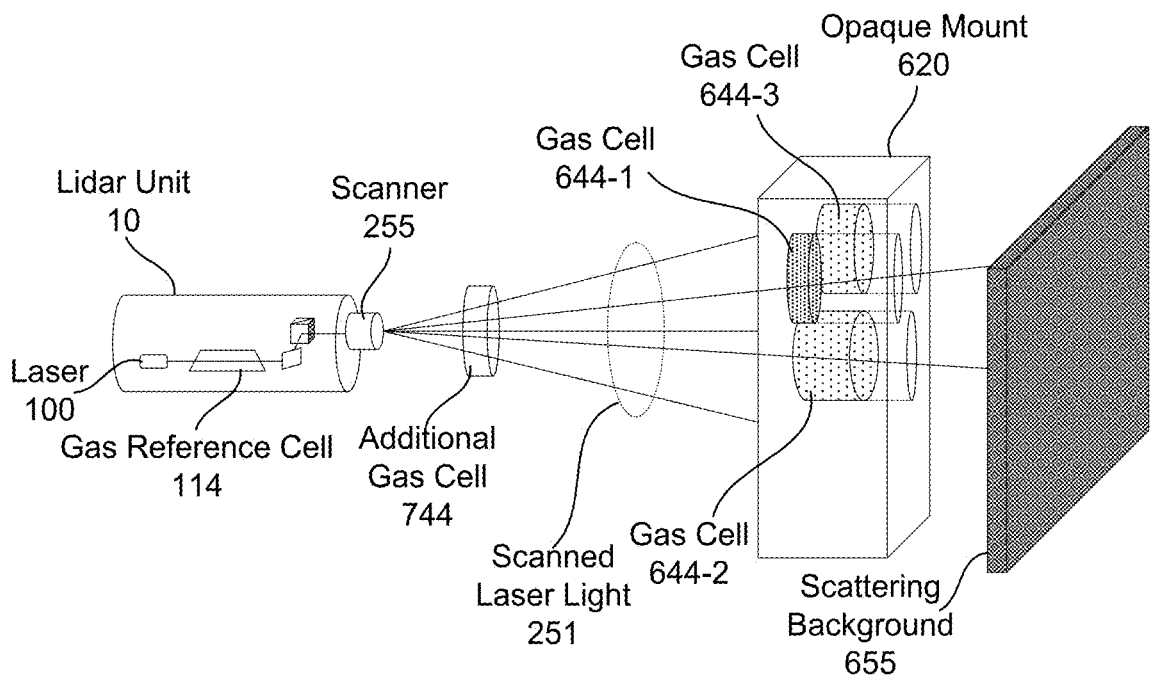

A representative optical layout for a method of calibrating a lidar transceiver system using external calibration cells is shown in FIG. 9 and FIGS. 10A and 10B. As in FIG. 1, a lidar transceiver system 10 is configured to shape light from a diode laser 100 and direct it as scanned laser light 251 into a scene. Scattered returning laser light 611 is collected by the transceiver and directed onto a detector 410.

As illustrated in FIGS. 9, 10A, and 10B, the lidar transceiver 10 also has an internal calibration gas reference cell 114 as described above. However, embodiments of an external calibration method that do not use an internal gas reference cell may also be implemented.

The "scene" of FIGS. 9, 10A, and 10B has placed within it a calibration unit 600 which, as illustrated, comprises an opaque mount 620 (typically painted flat black) in which a plurality of gas sample cells 644 are mounted. In some embodiments, each gas sample cell 644 is mounted in a hole formed within the opaque mount 620, such that light from the lidar unit may pass through each of the gas sample cells 644 but is otherwise absorbed by the opaque mount 620.

Each gas sample cell 644 is typically filled with a known, calibrated concentration of the gas of interest (for example, methane ($CH_4$) or carbon dioxide ($CO_2$)), and has a known and calibrated length between the centers of the windows. As with the gas reference cell 114 as described above, the windows of each of the gas sample cells 644 may be optically polished elements that are non-parallel and/or counter-beveled, and the two windows may also be arranged to have a counter-angled wedge configuration, to reduce multi-reflection interference effects. The windows of each of the gas sample cells may additionally be coated with anti-reflection (AR) coatings to further reduce reflections and possible interference effects.

The scanned laser light 251 that emerges from the lidar transceiver 10 passes through the gas sample cells 644 the calibration unit 600, and, on the far side of the calibration unit 600, will scatter off a scattering background 655. This is typically a piece of diffusing paper, semi-rigid foam, or posterboard that allows some light to be scattered back towards the lidar unit 10, but not a mirror or retroreflector that will reflect such a strong signal that the detector 410 may be overwhelmed.

In some embodiments, the scattering background 655 may feature multiple or changeable reflectivity in the scattering regions behind each cell. This may be used to test the lidar CPL measurement at multiple different signal levels, and to test for signal-related CPL measurement biases as discussed above.

Some portion of the scattered laser light 611 scatters back in the same direction from which it came, passing again through the gas sample cells 644 mounted in the opaque mount 620 of the calibration unit 600, and propagating back to the lidar unit 10. The external optics 218 and the return optics 418 allow returning photons to be directed towards the detector 410.

Light that emerges from the lidar unit 10 and passes through the environment of the calibration unit may additionally pass through some concentration of ambient gas 844 if some amount of the gas of interest is in the environment. The gas of interest is unlikely to be present in large amounts if detecting a toxic gas, however, carbon dioxide is a common environmental gas, and will be present in the atmosphere in most places on Earth, and ambient methane may be found in greater abundance around industrial facilities or agricultural feedlots.

The light from the laser 100 in the lidar unit 10 that finally arrives at the detector therefore a) passes through the gas reference cell 114 (if used), b) passes twice through the ambient gas 844 in the environment, and c) passes twice through the gas sample cells 644 mounted in the calibration unit 600.

When multiple gas reference cells 644, each having a different gas concentration and/or length, are used, and the lidar unit 10 is operated by scanning in wavelengths (as described above) while using a three-dimensional scanner 255 over the scene that allows multiple gas cells of the calibration unit to be imaged in one collected dataset, the lidar signals from different portions of the composite lidar image corresponding to the different gas sample cells can be used to determine the signal from known gas absorption contributions. Scanning the wavelength as described above therefore produces a different absorption dip for each of the gas sample cells, and the magnitudes of the dips can be combined with the known gas concentrations and lengths for the gas sample cells to calibrate the detected absorption computations.

When V three gas sample cells are used, there are therefore three values for absorption for the gas of interest that can be plotted and compared, corresponding to the laser paths through each of the three gas sample cells.

However, in a variation of the method, one or more additional (removable) gas sample cells 744 may be inserted in the beam path just outside the scanner. Such an additional gas cell 744 will also typically have non-parallel, counter-beveled windows, and may be coated with AR coatings to reduce reflections and interference fringes. The effect of the additional gas cell is 744 to introduce additional gas absorption for the laser beams, and therefore light that passes twice through the gas sample cells 644 also passes twice through the additional gas cell 744.

Comparison of gas absorption measurements with and without an additional gas sample cell doubles the number of calibration points available. Therefore, in a system using 3 gas sample cells, 3 calibration points are available. But in a system using 3 gas sample cells measured both with and without 1 additional (removable) gas cell, 6 calibration points are available.

To identify which portions of the lidar dataset correspond to which gas reference cells, some image processing may be needed to separate out lidar spectroscopy signals that only correspond to light respectively passing through each gas sample cells. To facilitate this image processing, some additional structural elements for the calibration unit 600 may be used.

Figure 11:
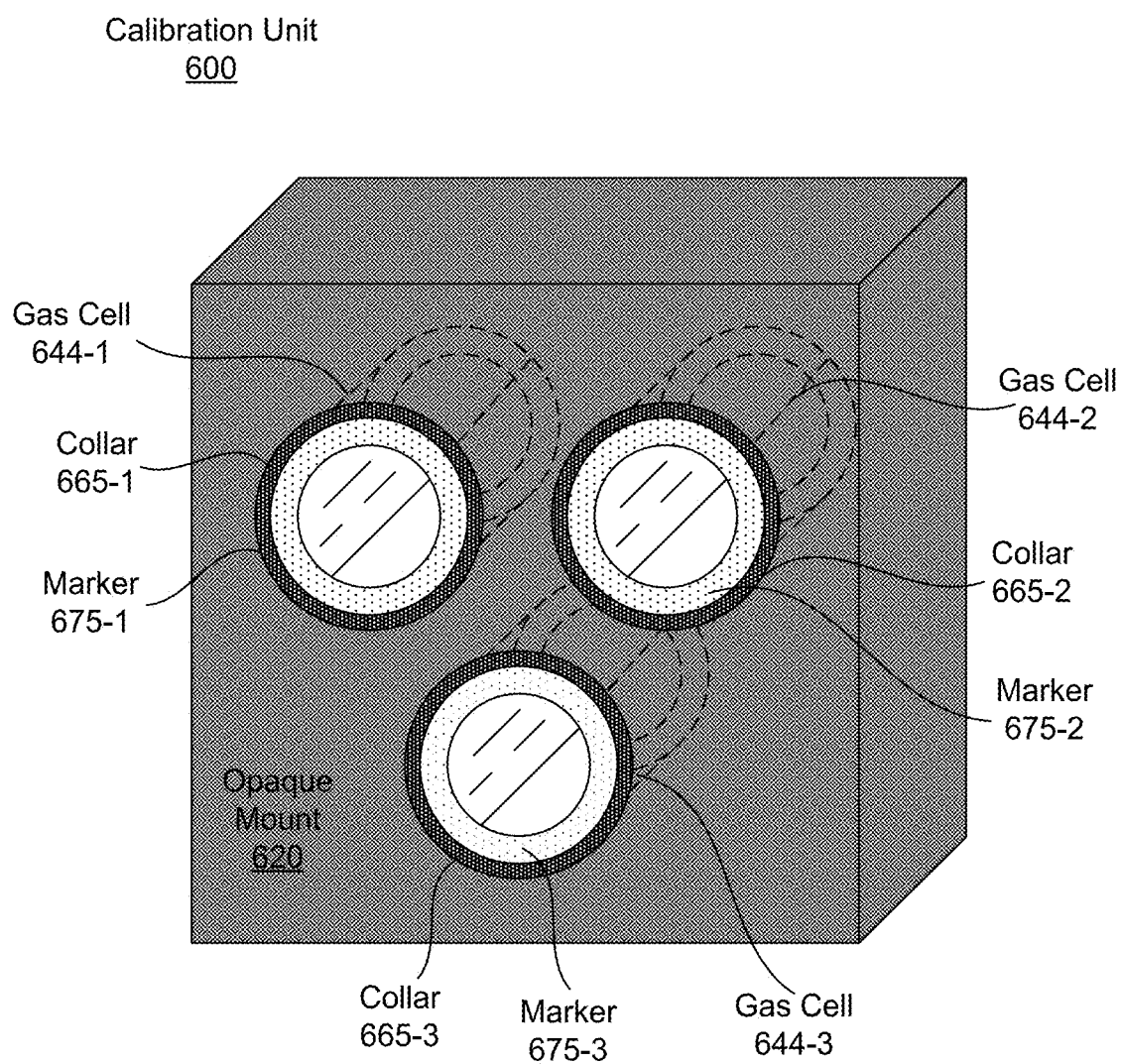
FIG. 11 illustrates a perspective view of the opaque mount and three external gas sample cells of FIG. 9.

As illustrated in FIG. 11, the gas sample cells may be placed in holes or apertures cut into the otherwise solid form of the opaque mount 620 of the calibration unit 600. Around the edge of the gas sample cells, collars 665 may be placed to both ensure that the gas sample cell is aligned and held securely within the calibration unit 600. On the side of these collars 665 facing the lidar unit 10, markers 675 that help to identify the boundary of each gas sample cell 644 may be placed. These markers 675 may be any marker that can be identified using various image processing algorithms on the collected data.

In some embodiments, the identifying markers 675 may comprise material that is more highly reflecting of the laser diode light, and so providing a bright return signal. In some embodiments, the identifying markers 675 may comprise reflective tape placed around each of the gas sample cells 644, to provide a circular pattern. The material should be chosen to yield a bright return signal, such that the cells can be easily identified against the rest of the observed scene.

Figure 12:
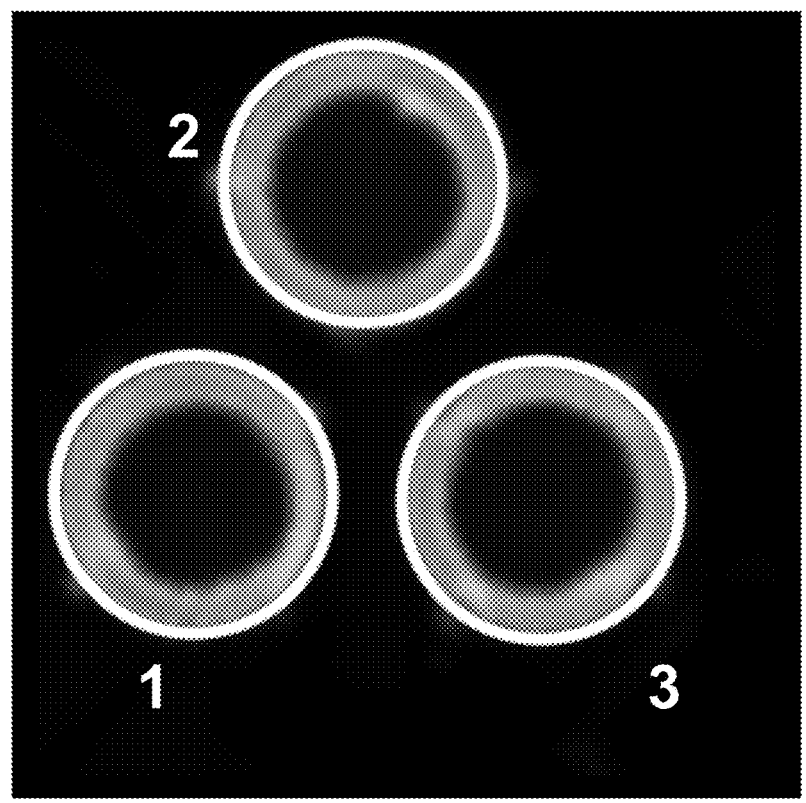
FIG. 12 illustrates a 2-D representation of lidar data from an arrangement comprising three external gas sample cells, with a) showing identifying markings indicating regions corresponding to gas sample cells for data collection, and b) indicating regions within the data from which spectroscopic values should be analyzed for a calibration procedure.
Figure 12:
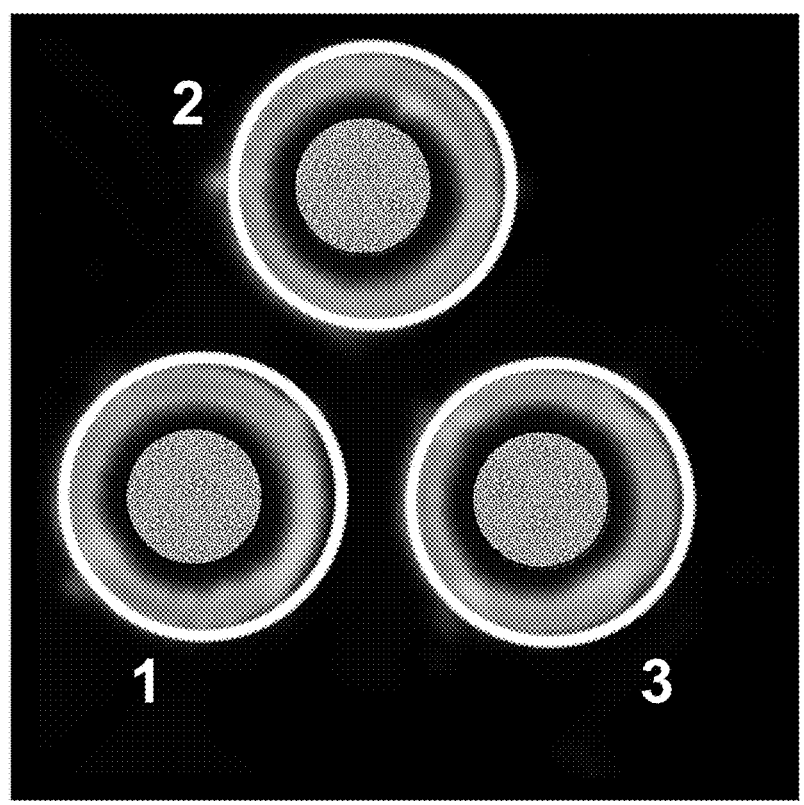

FIG. 12 illustrates a lidar image of a calibration unit having three gas sample cells, and using reflective tape as markers placed in a circular pattern on collars around each of the three gas sample cells, marked 1, 2, and 3. In the upper portion (identified as "a)"), the identifying markers stand out as bright return signals that can be used by image processing algorithms to identify regions within each circular pattern corresponding to particular gas sample cell. Examples of circular regions at the outer perimeter of the cells, identified through image processing algorithms, are illustrated as bright white circles.

Data from only the interior of the circular regions, as illustrated in the lower portion (identified as "b)"), provides a way to estimate gas absorption (typically presented as concentration path length (CPL) in parts-per-million meter (ppm-m) for the laser paths passing through the corresponding cell. The of the circular interior regions in FIG. 12 part b) are shown as pattern-filled circles, and represent the area from which CPL data may be calculated for the cell. The diameter in this illustration is 50% of the bright while circle identified from the outer perimeter of the identified markers, but may be defined as any pre-determined fraction in size or shape of the region identified as corresponding to the gas sample cell.

In some embodiments, multiple measurements collected from several points within each gas sample cell may be collected and averaged to produce a CPL value for the path through a sample cell.

Figure 13:
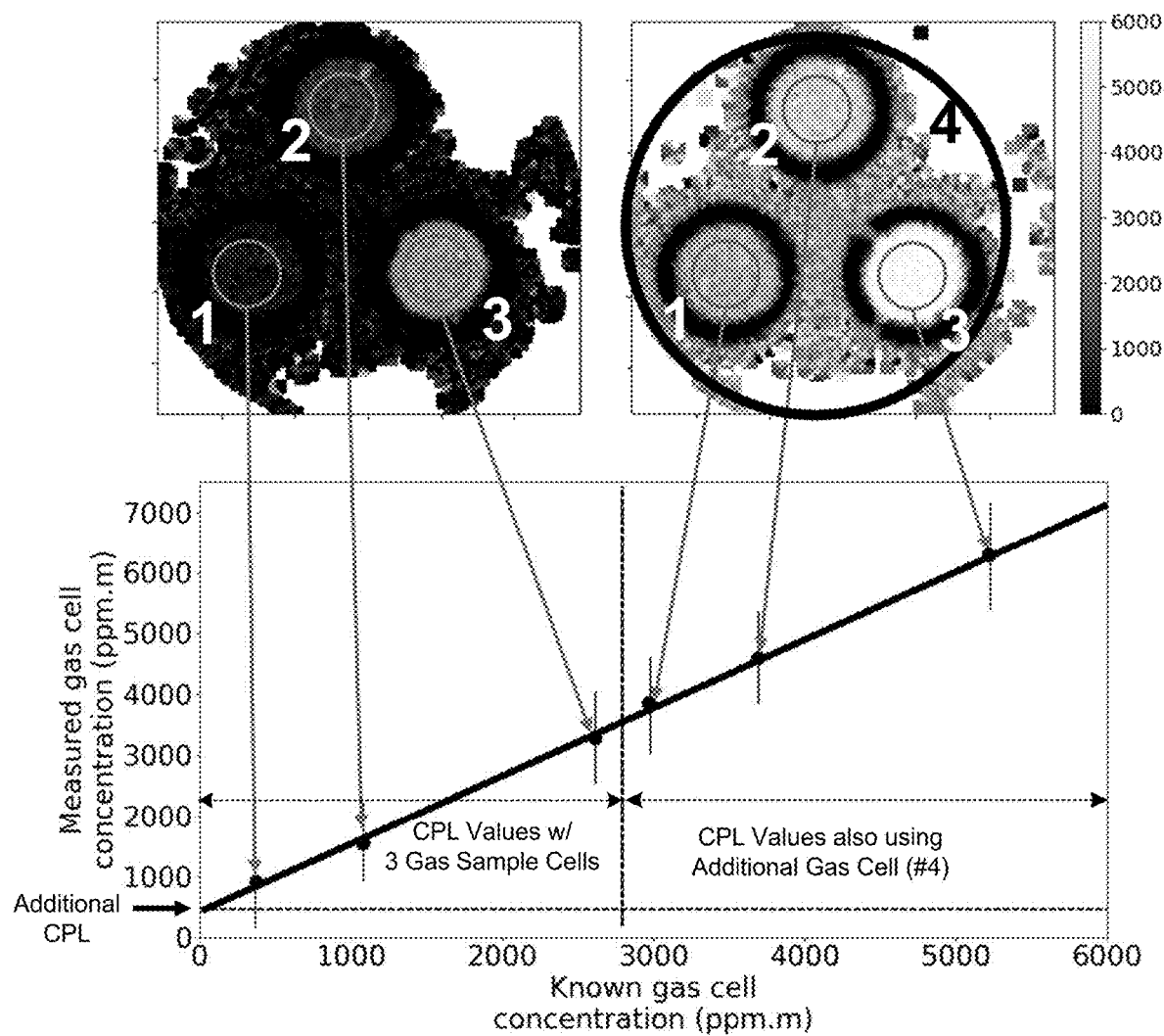
FIG. 13 illustrates a 2-D representation of lidar data from an arrangement comprising three external gas sample cells (upper left) and the same three cells with an additional gas cell (right), converted into a plot for the determination of CPL for the plurality of cells.

An example of plotting these CPL results for calibration for the lidar system is illustrated in FIG. 13. For the data presented in the plot, a calibration unit with three gas sample cells as was illustrated in FIGS. 9-11 was used to generate selected lidar image data for the three sample cells shown in the upper left portion of FIG. 13. The lengths and gas concentrations for the three sample cells are presented in Table II below, and the measured data for CPL corresponding to these regions, plotted against the nominal CPL expected from these cells, is illustrated in the lower part of FIG. 13.

After making one set of measurements using only the 3 sample cells in the calibration unit, a fourth, removable gas cell was then placed in front of the lidar unit, as was illustrated in FIG. 10B. Lidar image data for this additional situation is illustrated in the lidar image in the upper right side of FIG. 13. For the data presented in FIG. 13, the additional removable cell

TABLE II

Nominal CPL values for the example of FIG. 13.
Gas Sample Cell Dimensions

| | Length L | $CH_4$ Concentration | CPL = L × $C_{CH4}$ (ppm-m) |
|---|---|---|---|
| Gas Sample Cell 1 | 104.6 mm | 0.35% (3500 ppm) | 366 |
| Gas Sample Cell 2 | 309.2 mm | 0.35% (3500 ppm) | 1082 |
| Gas Sample Cell 3 | 104.6 mm | 2.5% (25000 ppm) | 2615 |
| Additional Removable Cell (Sample Cell 4) | 104.6 mm | 2.5% (25000 ppm) | +2615 | nominally had the same length and concentrations of sample cell 1 (also presented in Table II), and the measured data for CPL corresponding to the 3 gas sample cells with the additional contribution from the removable gas cell, plotted against the nominal CPL expected from this situation, is also illustrated in the plot in the lower part of FIG. 13.

With several data points for actual versus nominal CPL, a fit for the data can be computed. This function is typically a simple linear fit of the form $$\text{CPL(measured)} = m\ \text{CPL(nominal)} + C \qquad [\text{Eqn. 1}]$$

with m being the slope of the fit. Analysis may be carried out using any number of linear regression techniques, including dividing the data by the identified slope m and determining a coefficient of determination $R^2$. For the data illustrated in FIG. 13, $$\text{CPL(measured)} = 1.122\ \text{CPL(nominal)} + 421.34 \qquad [\text{Eqn. 2}]$$

with an $R^2$ of 0.999334. The additional CPL value is therefore (421.34 ppm-m).

This equation ideally will have an intercept at (0,0) (i.e. C=0; meaning no measured CPL due to absorption when no nominal CPL absorption present). However, when there is a positive value for C when CPL (Nominal)=0, as illustrated in the plot of FIG. 13, the additional CPL in the measured values can be interpreted as a contribution of (i) absorption from the internal gas reference cell (if being used in the lidar system), and/or (ii) additional ambient absorption from gas in the general environment.

If an internal gas reference cell is used and known, the contribution from the known gas reference cell can be additionally factored into the value of C, and the remaining portion of C attributed to CPL from ambient absorption in the environment:

$$C = C_{Ref} + C_{Ambient} \qquad [\text{Eqn. 3}]$$

Note: the gas reference cell used to collect the data described above had a one-pass CPL of approximately $C_{Ref}$=500 ppm-m. However, in calibration above, the linear fit results represent a correction for two passes through each gas sample cell, and are therefore divided by 2 to estimate CPL for each gas sample cell. The gas reference cell is only a single-pass contribution, so the subsequent division by 2 yields only 50% of the one-pass CPL, so $C_{Ref}$≈250 ppm-m. The remaining 171.34 ppm-m in the above example is attributable to $C_{Ambient}$.

Computation of the linear fit parameters of the measured CPL and nominal CPL can then be stored, and used in processing subsequent measurements of the lidar system in other environments.

Figure 14:
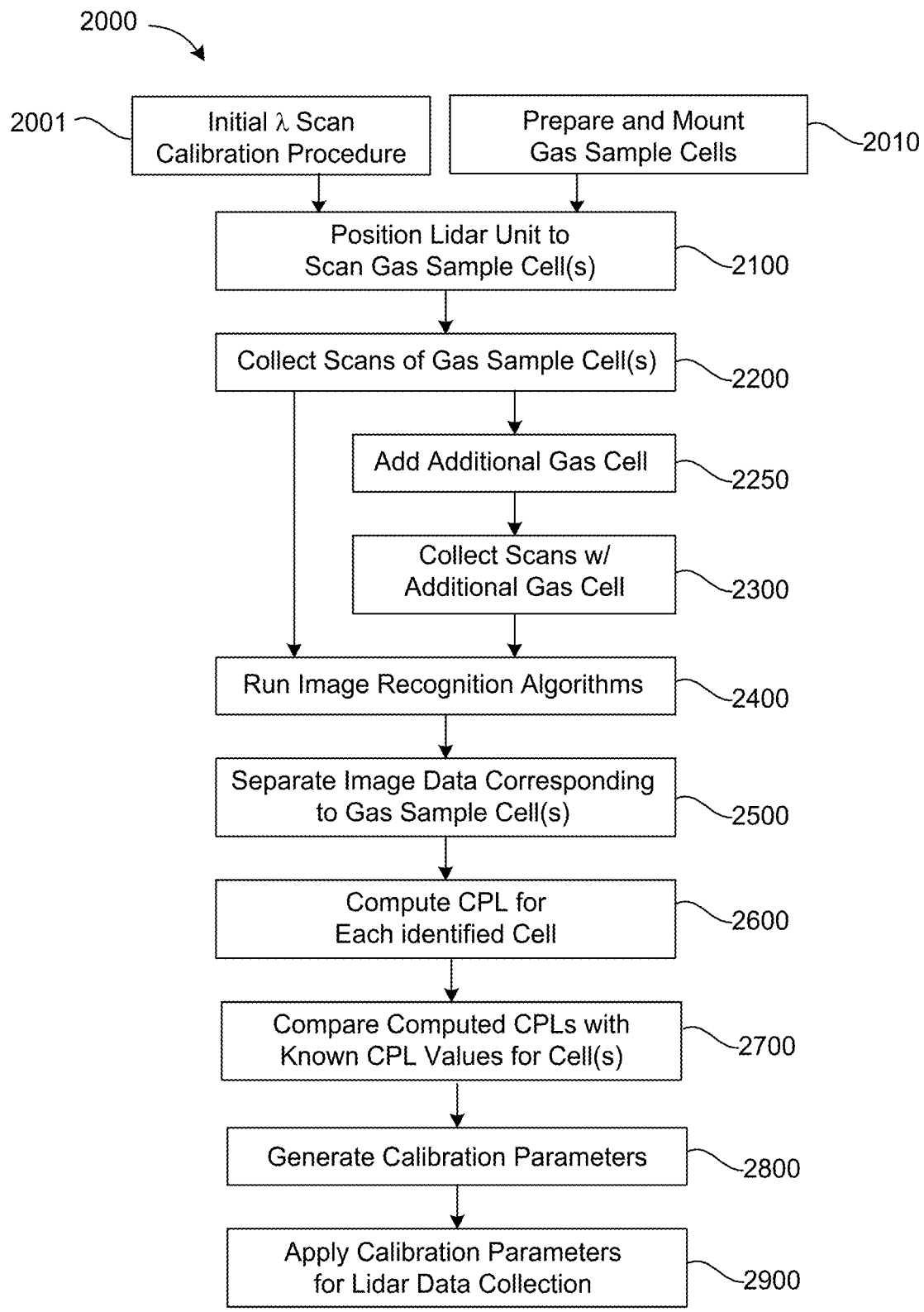
FIG. 14 illustrates a flow chart for a method of collecting data and calibrating CPL from a collection of external gas sample cells such as illustrated in FIGS. 9-13.

An example of a representative process 2000 to provide a calibration using one or more gas sample cells is presented in the flow chart of FIG. 14.

In the first operation 2001, the lidar system is turned on and initially adjusted so that the wavelength scans from the lidar system are overlapping with an absorption feature of a gas of interest. If the gas of interest is, for example methane ($CH_4$), the wavelength scan may be set to be around 1651 nm. If an internal gas reference cell is used in the lidar system, this initialization operation may reproduce in whole or in part the internal calibration procedure discussed above and illustrated in FIG. 7.

Meanwhile, in operation 2010, one or more gas sample cells may be placed in a calibration unit and mount, as described above and illustrated in, for example, FIGS. 10A, 10B, and 11. In some embodiments, the gas cells may be prepared by confirming the cell length and filling them with a known concentration of the gas of interest. In some embodiments, pre-calibrated gas cells with already known concentrations of the gas of interest may be used. In some embodiments, the gas sample cells as mounted may have ports and stopcocks that allow the gas concentration to be set or adjusted during calibration. In some embodiments, some or all of the gas sample cells are additionally provided with identifying markers that allow the cells to be recognized and identified using image processing programs.

In the next operation 2100, the lidar system is positioned relative to the calibration unit having one or more gas sample cells such that some or all of the gas sample cells can be scanned by the lidar system. This operation may also involve placement of a scattering object, such as a cardboard or foam sheet, on the far side of the calibration unit, to provide scattering sites that return a signal to the lidar system that can be collected on the detector.

In the next operation 2200, one or more lidar scans of the scene including the gas sample cells of the calibration unit are made. The lidar scan may involve both scans in wavelength, as discussed above, and scans in angle over the scene to form a two-dimensional image. Laser light from the lidar system passes through the gas sample cells, scatters from scattering points in the scattering object, and returns in a second pass through the gas sample cells and the lidar data collected and correlated with the wavelength scans. The scanned lidar data may be formatted and represented as two-dimensional imaging data for internal use and for subsequent data processing operations.

If only data from the gas sample cells mounted in the calibration unit are to be collected, then the process will move ahead to operation 2400. However, if additional data using an additional removable gas cell will be collected, then in the next operation 2350, the additional removable gas cell is inserted in front of the lidar unit such that all scanned laser output from the lidar unit also passes through the removable gas cell.

In the next operation 2300, one or more lidar scans of the scene with the calibration unit are made, but now also including the additional gas cell. The additional lidar data are collected and also correlated with the wavelength scans. The lidar data may be stored in the format of two-dimensional images, with each pixel corresponding to a particular angle set by the scanner.

In operation 2400, the collected lidar imaging data is processed and, in some embodiments, pattern recognition algorithms run on the detected signal data to identify markers corresponding to regions containing data from transmission through gas cells of the calibration unit. Such markers may be circles of reflecting tape, as was illustrated in FIG. 13, strategically placed bar codes or QR codes, or other identifying marks that can be detected using contemporary image processing techniques.

In the next operation 2500, further pattern recognition operations are carried out on the lidar data to separate or isolate portions of the data corresponding to the various detected gas sample cells.

In the next operation 2600, using the wavelength scans and the separated portions of the data corresponding to each of the identified gas sample cells in the calibration unit, an analysis for each identified cell is carried out, and the reduction in return signal corresponding to absorption by the gas of interest is determined for each identified cell. Then, using the known length of the cell, values for CPL in ppm-m for the gas of interest are calculated for each identified cell. These may assume a double pass through each gas sample cell as well as the additional gas cell (if used) (i.e. effective length will be twice the physical length), and may involve averaging multiple locations within each gas sample cell together to produce a composite CPL value for the cell.

In the next operation 2700, the calculated values for CPL for each of the gas sample cells as determined from the measured lidar data are compared to the nominal values for CPL expected using the known lengths and concentrations of the gas sample cell(s) (and the additional gas cell(s), if used).

In the next operation 2800, the mathematical relationship between the nominal CPL and the measured CPL is determined. This is typically a linear fit, but other functions may be used as well. Various parameters or calibration factors needed to align the nominal and measured values are determined in this operation as well.

The typical linear fit of measured CPL against nominal CPL yields a metric of the linearity of the lidar CPL measurement, in the form of the R-Squared ($R^2$) value. This linearity measure may be used as a quality indicator of the lidar CPL measurement accuracy and precision. It may also be used to indicate as to whether other issues are present in the lidar, such as imperfect wavelength calibration, insufficient signal, or spurious noise impacting the CPL measurement.

If the fit is poor or show significant nonlinearity, or otherwise differs from expected values by more than some predetermined amount, the parameters used in calculating CPL for the gas sample cells may be adjusted, and the process for calculation of CPL from the lidar data run again using the revised parameters.

In the next operation 2900, once the calibration parameters have been generated, they may be programed into the analysis programming of the lidar system, and the lidar unit may then be used in the field to collect scans of scenes without having the calibration unit present.

Once calibration parameters have been programmed into the lidar per operation 2900, the entire process beginning in operation 2001 or 2100, and ending in operation 2800, may be repeated in order to confirm successful calibration.

Similarly, the entire process beginning in operation 2001 or 2100, and ending in operation 2800, may be repeated at times throughout the deployment of the lidar system in order to measure and calibrate ongoing performance. This may be performed either in the field with a mobile assembly of gas sample cells, or through return of the lidar unit to measure a fixed assembly of cells a laboratory setting.

Other Implementations and Clauses

The descriptions above have disclosed embodiments in which methane ($CH_4$) is the gas of interest, and calibrating a lidar system to more accurately detect and quantify leaks at a facility processing methane may be one possible application of the disclosed technology. However, as discussed above, other gasses of interest may be detected using the technology described in this disclosure, including carbon dioxide ($CO_2$), ammonia ($NH_3$), ethylene ($C_2H_4$), hydrogen sulfide ($H_2S$), or any number of other volatile organic compounds or hydrocarbons that have absorption features coincident with diode wavelengths that are tunable and compatible with a lidar system.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations. Other implementations may include systems that may incorporate a non-transitory computer readable storage medium storing instructions executable by a processor to perform functions described above. Yet another implementation may include a method performing the functions described above in a system.

The terms and expressions employed herein are used as terms and expressions of description and not of limitation, and there is no intention, in the use of such terms and expressions, of excluding any equivalents of the features shown and described or portions thereof. In addition, having described certain implementations of the technology disclosed, it will be apparent to those of ordinary skill in the art that other implementations incorporating the concepts disclosed herein can be used without departing from the spirit and scope of the technology disclosed. Accordingly, the described implementations are to be considered in all respects as only illustrative and not restrictive.

A number of flowcharts are described herein. The logic within these flowcharts can be implemented using processors programmed using computer programs stored in memory accessible to the computer systems and executable by the processors, by dedicated logic hardware, including field programmable integrated circuits, and by combinations of dedicated logic hardware and computer programs. With all flowcharts herein, it will be appreciated that many of the steps can be combined, performed in parallel or performed in a different sequence without affecting the functions achieved. In some cases, a re-arrangement of steps will achieve the same results only if certain other changes are made as well. In other cases, a re-arrangement of steps will achieve the same results only if certain conditions are satisfied. Furthermore, it will be appreciated that the flowcharts herein show only steps that are pertinent to an understanding of the disclosed technology, and it will be understood that numerous additional steps for accomplishing other functions can be performed before, after and between those shown.

A number of clauses are disclosed below. One or more implementations and clauses of the technology disclosed or elements thereof can be implemented in the form of a computer product, including a non-transitory computer readable storage medium with computer usable program code for performing the method steps indicated. Furthermore, one or more implementations and clauses of the technology disclosed or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. It will be understood how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

We disclose the following numbered clauses:

1. A method of calibrating a lidar system for detecting a gas, the method comprising:
in a lidar system comprising a tunable laser and a gas reference cell, wherein temperature of the tunable laser is controlled electronically using a thermoelectric cooler and wavelength for the tunable laser is adjustable by changing an electric drive current for the laser, and wherein the gas reference cell contains a predetermined concentration of a gas to be detected,
directing output of the tunable laser to pass through the gas reference cell to one or more scattering points;
scanning the drive current so that the laser produces laser light over a spectrum of wavelengths, wherein points of time of the scan have a predetermined relationship to the drive current and the spectrum of wavelengths;
detecting returning laser light scattered from the scattering points over a period of time and correlating the detected returning laser light to the spectrum of wavelengths;
analyzing the correlation of the detected returning laser light to detect a reduction in signal corresponding to at least one wavelength within the spectrum of wavelengths; and
adjusting the temperature of the tunable laser so that the reduction in signal corresponds to a drive current in the middle of the scan.

2. The method of clause 1, wherein
the at least one wavelength within the spectrum of wavelengths corresponding to the reduction in signal also corresponds to an absorption wavelength for the gas in the gas reference cell.

3. The method of either clause 1 or 2, wherein
when the reduction in signal corresponding to a at least one wavelength within the spectrum of wavelengths corresponds to a lower current,
the method includes adjusting the temperature of the tunable laser represents an increase in temperature.

4. The method of any preceding clause, wherein
when the reduction in signal corresponding to at least one wavelength within the spectrum of wavelengths corresponds to a higher current,
the method includes adjusting the temperature of the tunable laser represents a decrease in temperature.

5. The method of any preceding clause, wherein
the tunable laser is a distributed feedback diode laser.

6. The method of any preceding clause, wherein
the gas to be detected is methane ($CH_4$).

7. The method of any preceding clause, wherein
the predetermined concentration in the gas reference cell of the gas to be detected is 5%, with the cell otherwise containing nitrogen gas ($N_2$).

8. The method of any preceding clause, wherein
the tunable laser is a distributed feedback diode laser designed to operate at a wavelength of 1651 nm.

9. The method of any preceding clause, wherein
the gas reference cell has two non-parallel windows, each with a center region, and with each of the windows having two non-parallel surfaces; and
the method includes directing output of the tunable laser to pass through the gas reference cell comprises directing the output through the center regions of the two non-parallel windows.

10. The method of any preceding clause, wherein
the two non-parallel windows are counter-beveled, with one of the windows at an angle of approximately 87 degrees from a line connecting the window centers and the other window at an angle of approximately −87 degrees from said line; and wherein the two non-parallel surfaces of each of the two non-parallel windows have a wedge angle greater than 0.2 degrees, and wherein
each of the two non-parallel windows is coated with an anti-reflection coating.

11. A method of calibrating a lidar system for detecting a gas, method comprising:

in a lidar system comprising a tunable laser, the tunable laser set to change wavelength over a spectrum that encompasses a wavelength of absorption for a gas to be detected, directing output of the tunable laser to pass through an assembly of one or more gas sample cells to one or more scattering points, each of the one or more gas sample cell having a predetermined concentration of the gas to be detected and each of the one or more gas sample cells having an identifying marker;

scanning the laser wavelength over a spectrum of wavelengths, wherein points of time of the scan have a predetermined relationship to the spectrum of wavelengths;

generating signal data by detecting returning laser light scattered from the scattering points over a period of time;

running pattern recognition on the detected signal data to determine portions of the signal data corresponding to returning laser light that has passed through at least one gas sample cell and scattered off at least one of the scattering points;

for the portions of the signal data corresponding to returning laser light that has passed through at least one gas sample cell and scattered off at least one scattering point, detecting returning laser light scattered from the scattering points over the period of time and correlating the detected returning laser light to the spectrum of wavelengths;

analyzing the correlation of the detected returning laser light to detect a reduction in signal corresponding to at least one wavelength of absorption for the gas to be detected;

calculating, from a magnitude of the reduction in signal, an estimate of the absorption of the laser light along a path to the scattering point and back as a concentration path length (CPL) in ppm-m;

comparing the calculated estimate of the absorption with a known concentration of gas in the at least one gas sample cell.

12. The method of clause 11, additionally comprising:
if the comparison between the calculated estimate of the absorption with the known concentration of gas in the at least one gas sample cell differs by more than a predetermined amount,
adjusting parameters used in calculating the estimate of the absorption;
calculating, from the magnitude of the reduction in signal and using the adjusted parameters, a revised estimate of the absorption of the laser light along the path to the scattering point and back as a concentration path length (CPL) in ppm-m; and
comparing the revised estimate of the absorption with the known concentration of gas in the at least one gas sample cell.

13. The method of any of clauses 11 through 12, wherein the tunable laser is a distributed feedback diode laser.

14. The method of any of clauses 11 through 13, wherein the gas to be detected is methane ($CH_4$), and
the tunable laser is a distributed feedback diode laser designed to operate at a wavelength of 1651 nm.

15. The method of any of clauses 11 through 14, wherein the predetermined concentration of the gas in each cell produces an CPL for each cell between 100 ppm-m and 500,000 ppm-m.

16. The method of any of clauses 11 through 15,
wherein the assembly has a plurality of gas sample cells, each with a different CPL for the gas to be detected, and
wherein a plurality of measured CPLs for the plurality of gas sample cells are used to determine an ambient absorption.

17. The method of any of clauses 11 through 16, additionally comprising:
inserting an additional gas cell with a known concentration of the gas to be detected between the tunable laser and the assembly of one or more gas sample cells;
again directing the output of the tunable laser to pass through an assembly of one or more gas sample cells to one or more scattering points;
again scanning the laser wavelength over a spectrum of wavelengths, wherein points of time of the scan have a predetermined relationship to the spectrum of wavelengths;
again generating signal data by detecting returning laser light scattered from the scattering points over a period of time;
again running pattern recognition on the detected signal data to determine portions of the signal data corresponding to returning laser light that has passed through at least one gas sample cell and scattered off at least one of the scattering points;
for the portions of the signal data corresponding to returning laser light that has passed through at least one gas sample cell and scattered off at least one scattering point,
again detecting returning laser light scattered from the scattering points over the period of time and correlating the detected returning laser light to the spectrum of wavelengths;
again analyzing the correlation of the detected returning laser light to detect a reduction in signal corresponding to at least one wavelength of absorption for the gas to be detected; and
again calculating, from magnitude of the reduction in signal, an estimate of the absorption of the laser light along the path to the scattering point and back as a concentration path length (CPL) in ppm-m;
comparing the calculated estimate of the absorption with the known concentration of gas in the additional gas cell and in the at least one gas sample cell;
if the comparison between the calculated estimate of the absorption with the known concentration of gas in the at least one gas cell differs by more than a predetermined amount,
adjusting parameters used in calculating the estimate of the absorption;
calculating, from the magnitude of the reduction in signal and the adjusted parameters, a revised estimate of the absorption of the laser light along the path to the scattering point and back as a concentration path length (CPL) in ppm-m; and
comparing the revised estimate of the CPL with the known concentration of gas in the at least one gas cell.

18. The method of any of clauses 11 through 17,
wherein the assembly has a plurality of gas sample cells, each with a different CPL for the gas to be detected; and
wherein a plurality of measured CPLs for the plurality of gas sample cells, along with the measured CPLs with the additional gas cell, are used to determine an ambient absorption.

19. The method of any of clauses 11 through 18,
wherein the gas sample cells in the assembly have edges that are approximately circular cylinders in shape, and the identifying markers for each gas cell comprise reflective material forming a circular outline at the edges of the gas sample cell.

20. The method of clause 1 carried out concurrently with, or prior to, executing the method of clause 12.

21. A lidar system for detecting a gas, comprising a tunable laser and a gas reference cell, wherein temperature of the tunable laser is controlled electronically using a thermoelectric cooler and wavelength for the tunable laser is adjustable by changing an electric drive current for the laser, and wherein the gas reference cell contains a predetermined concentration of a gas to be detected, and including one or more processors including or having access to memory loaded with computer instructions that, when executed on the one or more processors, implement actions comprising:

directing output of the tunable laser to pass through the gas reference cell to one or more scattering points;

scanning the drive current so that the laser produces laser light over a spectrum of wavelengths, wherein points of time of the scan have a predetermined relationship to the drive current and the spectrum of wavelengths;

detecting returning laser light scattered from the scattering points over a period of time and correlating the detected returning laser light to the spectrum of wavelengths;

analyzing the correlation of the detected returning laser light to detect a reduction in signal corresponding to at least one wavelength within the spectrum of wavelengths; and adjusting the temperature of the tunable laser so that the reduction in signal corresponds to a drive current in the middle of the scan.

22. A lidar system for detecting a gas comprising a tunable laser, the tunable laser set to change wavelength over a spectrum that encompasses a wavelength of absorption for a gas to be detected, and including one or more processors including or having access to memory loaded with computer instructions that, when executed on the one or more processors, implement actions comprising:

directing output of the tunable laser to pass through an assembly of one or more gas sample cells to one or more scattering points, each of the one or more gas sample cell having a predetermined concentration of the gas to be detected and each of the one or more gas sample cells having an identifying marker;

scanning the laser wavelength over a spectrum of wavelengths, wherein points of time of the scan have a predetermined relationship to the spectrum of wavelengths;

generating signal data by detecting returning laser light scattered from the scattering points over a period of time;

running pattern recognition on the detected signal data to determine portions of the signal data corresponding to returning laser light that has passed through at least one gas sample cell and scattered off at least one of the scattering points;

for the portions of the signal data corresponding to returning laser light that has passed through at least one gas sample cell and scattered off at least one scattering point, detecting returning laser light scattered from the scattering points over the period of time and correlating the detected returning laser light to the spectrum of wavelengths;

analyzing the correlation of the detected returning laser light to detect a reduction in signal corresponding to at least one wavelength of absorption for the gas to be detected;

calculating, from a magnitude of the reduction in signal, an estimate of the absorption of the laser light along a path to the scattering point and back as a concentration path length (CPL) in ppm-m;

comparing the calculated estimate of the absorption with a known concentration of gas in the at least one gas sample cell;

if the comparison between the calculated estimate of the absorption with the known concentration of gas in the at least one gas sample cell differs by more than a predetermined amount, adjusting parameters used in calculating the estimate of the absorption;

calculating, from the magnitude of the reduction in signal and using the adjusted parameters, a revised estimate of the absorption of the laser light along the path to the scattering point and back as a concentration path length (CPL) in ppm-m; and comparing the revised estimate of the absorption with the known concentration of gas in the at least one gas sample cell.

23. A lidar system for detecting a gas, comprising:
a tunable laser;
a thermoelectric cooler;
a gas reference cell;
wherein temperature of the tunable laser is controlled electronically using the thermoelectric cooler, and wavelength for the tunable laser is adjustable by changing an electric drive current for the laser, and wherein the gas reference cell contains a predetermined concentration of a gas to be detected; and one or more processors including or having access to memory loaded with computer instructions that, when executed on the one or more processors, implement actions comprising:

directing output of the tunable laser to pass through the gas reference cell to one or more scattering points;

scanning the drive current so that the laser produces laser light over a spectrum of wavelengths, wherein points of time of the scan have a predetermined relationship to the drive current and the spectrum of wavelengths;

detecting returning laser light scattered from the scattering points over a period of time and correlating the detected returning laser light to the spectrum of wavelengths;

analyzing the correlation of the detected returning laser light to detect a reduction in signal corresponding to at least one wavelength within the spectrum of wavelengths; and adjusting the temperature of the tunable laser so that the reduction in signal corresponds to a drive current in the middle of the scan.

24. A method of any of clauses 1 through 23, wherein the gas reference cell has a concentration of a gas of interest traceable to a gas concentration standard.

25. A method or system executing any of the operations of clauses 1 through 24 in combination with any of the other operations of clauses 1 through 24.

While the technology disclosed is disclosed by reference to the preferred implementations and examples detailed above, it is to be understood that these examples are intended in an illustrative rather than in a limiting sense. It is contemplated that modifications and combinations will readily occur to those skilled in the art, which modifications and combinations will be within the spirit of the innovation and the scope of the following claims.

What is claimed is:

1. A method of calibrating a lidar system for detecting a gas, the method comprising:
   in a lidar system comprising a tunable laser and a gas reference cell, wherein temperature of the tunable laser is controlled electronically using a thermoelectric cooler and wavelength for the tunable laser is adjustable by changing an electric drive current for the laser, and wherein the gas reference cell contains a predetermined concentration of a gas to be detected,
   directing output of the tunable laser to pass through the gas reference cell to one or more scattering points;
   scanning the drive current so that the laser produces laser light over a spectrum of wavelengths, wherein points of time of the scan have a predetermined relationship to the drive current and the spectrum of wavelengths;
   detecting returning laser light scattered from the scattering points over a period of time and correlating the detected returning laser light to the spectrum of wavelengths;
   analyzing the correlation of the detected returning laser light to detect a reduction in signal corresponding to at least one wavelength within the spectrum of wavelengths; and
   adjusting the temperature of the tunable laser so that the reduction in signal corresponds to a drive current in the middle of the scan, thereby calibrating the lidar system.

2. The method of claim 1, wherein
   the at least one wavelength within the spectrum of wavelengths corresponding to the reduction in signal also corresponds to an absorption wavelength for the gas in the gas reference cell.

3. The method of claim 1, wherein
   when the reduction in signal corresponding to at least one wavelength within the spectrum of wavelengths corresponds to a lower current,
   the method includes adjusting the temperature of the tunable laser represents an increase in temperature.

4. The method of claim 1, wherein
   when the reduction in signal corresponding to at least one wavelength within the spectrum of wavelengths corresponds to a higher current,
   the method includes adjusting the temperature of the tunable laser represents a decrease in temperature.

5. The method of claim 1, wherein
   the tunable laser is a distributed feedback diode laser.

6. The method of claim 1, wherein
   the gas to be detected is methane ($CH_4$).

7. The method of claim 6, wherein
   the predetermined concentration in the gas reference cell of the gas to be detected is 5%, with the cell otherwise containing nitrogen gas ($N_2$).

8. The method of claim 7, wherein
   the tunable laser is a distributed feedback diode laser designed to operate at a wavelength of 1651 nm.

9. The method of claim 1, wherein
   the gas reference cell has two non-parallel windows, each with a center region, and with each of the windows having two non-parallel surfaces; and
   the method includes directing output of the tunable laser to pass through the gas reference cell comprises directing the output through the center regions of the two non-parallel windows.

10. The method of claim 9, wherein
    the two non-parallel windows are counter-beveled, with one of the windows at an angle of approximately 87 degrees from a line connecting the window centers and the other window at an angle of approximately −87 degrees from said line; wherein
    the two non-parallel surfaces of each of the two non-parallel windows have a wedge angle greater than 0.2 degrees; and wherein
    each of the two non-parallel windows is coated with an anti-reflection coating.

11. A method of calibrating a lidar system for detecting a gas, method comprising:
    in a lidar system comprising a tunable laser, the tunable laser set to change wavelength over a spectrum that encompasses a wavelength of absorption for a gas to be detected,
    directing output of the tunable laser to pass through an assembly of one or more gas sample cells to one or more scattering points, each of the one or more gas sample cells having a predetermined concentration of the gas to be detected and each of the one or more gas sample cells having an identifying marker;
    scanning the laser wavelength over a spectrum of wavelengths, wherein points of time of the scan have a predetermined relationship to the spectrum of wavelengths;
    generating signal data by detecting returning laser light scattered from the scattering points over a period of time;
    running pattern recognition on the detected signal data to determine portions of the signal data corresponding to the identifying markers, and to determine portions of the signal data corresponding to returning laser light that has passed through at least one gas sample cell and scattered off at least one of the scattering points;
    for the portions of the signal data corresponding to returning laser light that has passed through at least one gas sample cell and scattered off at least one scattering point,
    detecting returning laser light scattered from the scattering points over the period of time and correlating the detected returning laser light to the spectrum of wavelengths;
    analyzing the correlation of the detected returning laser light to detect a reduction in signal corresponding to at least one wavelength of absorption for the gas to be detected;
    calculating, from a magnitude of the reduction in signal, an estimate of the absorption of the laser light along a path to the scattering point and back as a concentration path length (CPL) in ppm-m;
    comparing the calculated estimate of the absorption with a known concentration of gas in the at least one gas sample cell; and
    calculating calibration factors needed to align the known concentration of gas and the calculated estimate of the absorption, thereby calibrating the lidar system.

12. The method of claim 11, additionally comprising:
    when the comparison between the calculated estimate of the absorption with the known concentration of gas in the at least one gas sample cell differs by more than a predetermined amount,
    adjusting the calibration factors;
    calculating, from the magnitude of the reduction in signal and using the adjusted calibration factors, a revised estimate of the absorption of the laser light along the path to the scattering point and back as a CPL in ppm-m; and comparing the revised estimate of the absorption with the known concentration of gas in the at least one gas sample cell; and when the comparison between the revised estimate of the absorption with the known concentration of gas in the at least one gas sample cell is within a predetermined amount, programming the adjusted calibration factors into analysis programming of the lidar system.

13. The method of claim 11, wherein
the tunable laser is a distributed feedback diode laser.

14. The method of claim 11, wherein
the gas to be detected is methane ($CH_4$), and
the tunable laser is a distributed feedback diode laser designed to operate at a wavelength of 1651 nm.

15. The method of claim 11, wherein
the predetermined concentration of the gas in each cell produces a CPL for each cell between 100 ppm-m and 500,000 ppm-m.

16. The method of claim 11,
wherein the assembly has a plurality of gas sample cells, each with a different CPL for the gas to be detected, and
wherein a plurality of measured CPLs for the plurality of gas sample cells are used to determine an ambient absorption.

17. The method of claim 11, additionally comprising:
inserting an additional gas cell with a known concentration of the gas to be detected between the tunable laser and the assembly of one or more gas sample cells;
directing the output of the tunable laser to pass through the additional gas cell and the assembly of one or more gas sample cells to one or more scattering points;
again scanning the laser wavelength over a spectrum of wavelengths, wherein points of time of the scan have a predetermined relationship to the spectrum of wavelengths;
again generating signal data by detecting returning laser light scattered from the scattering points over a period of time;
again running pattern recognition on the detected signal data to determine portions of the signal data corresponding to the identifying markers, and to determine portions of the signal data corresponding to returning laser light that has passed through at least one gas sample cell and scattered off at least one of the scattering points;
for the portions of the signal data corresponding to returning laser light that has passed through at least one gas sample cell and scattered off at least one scattering point,
again detecting returning laser light scattered from the scattering points over the period of time and correlating the detected returning laser light to the spectrum of wavelengths;
again analyzing the correlation of the detected returning laser light to detect a reduction in signal corresponding to at least one wavelength of absorption for the gas to be detected; and
again calculating, from magnitude of the reduction in signal, an estimate of the absorption of the laser light along the path to the scattering point and back as a CPL in ppm-m;

comparing the calculated estimate of the absorption with the known concentration of gas in the additional gas cell and in the at least one gas sample cell;

again calculating calibration factors needed to align the known concentration of gas and the calculated CPL; and when the comparison between the calculated estimate of the absorption with the known concentration of gas in the at least one gas sample cell is within a predetermined amount, programming the calibration factors into the analysis programming of the lidar system; whereas when the comparison between the calculated estimate of the absorption with the known concentration of gas in the at least one gas cell differs by more than a predetermined amount, adjusting the calibration factors;

calculating, from the magnitude of the reduction in signal and the adjusted calibration factors, a revised estimate of the absorption of the laser light along the path to the scattering point and back as a CPL in ppm-m; and comparing the revised estimate of the absorption with the known concentration of gas in the at least one gas cell; and when the comparison between the revised estimate of the absorption with the known concentration of gas in the at least one gas sample cell is within a predetermined amount, programming the adjusted calibration factors into the analysis programming of the lidar system.

18. The method of claim 17,
wherein the assembly has a plurality of gas sample cells, each with a different CPL for the gas to be detected; and
wherein a plurality of measured CPLs for the plurality of gas sample cells, along with the measured CPLs with the additional gas cell, are used to determine an ambient absorption.

19. The method of claim 11,
wherein the gas sample cells in the assembly have edges that are approximately circular cylinders in shape, and the identifying markers for each gas cell comprise reflective material forming a circular outline at the edges of the gas sample cell; and wherein
running pattern recognition on the detected signal data to determine portions of the signal data corresponding to the identifying markers comprises
recognizing circular patterns in the signal data corresponding the circular outlines.

20. A lidar system for detecting a gas, comprising:
a tunable laser;
a thermoelectric cooler;
a gas reference cell;
wherein temperature of the tunable laser is controlled electronically using the thermoelectric cooler, and wavelength for the tunable laser is adjustable by changing an electric drive current for the laser, and wherein the gas reference cell contains a predetermined concentration of a gas to be detected; and
one or more processors including or having access to a non-transitory computer readable storage medium loaded with computer instructions that, when executed on the one or more processors, implement actions comprising:
directing output of the tunable laser to pass through the gas reference cell to one or more scattering points;
scanning the drive current so that the laser produces laser light over a spectrum of wavelengths, wherein points of time of the scan have a predetermined relationship to the drive current and the spectrum of wavelengths;

detecting returning laser light scattered from the scattering points over a period of time and correlating the detected returning laser light to the spectrum of wavelengths;

analyzing the correlation of the detected returning laser light to detect a reduction in signal corresponding to at least one wavelength within the spectrum of wavelengths; and adjusting the temperature of the tunable laser so that the reduction in signal corresponds to a drive current in the middle of the scan.

* * * * *